(12) United States Patent
Bartic et al.

(10) Patent No.: US 7,991,465 B2
(45) Date of Patent: Aug. 2, 2011

(54) MEANS FOR FUNCTIONAL RESTORATION OF A DAMAGED NERVOUS SYSTEM

(75) Inventors: Carmen Bartic, Wilsele (BE); Jean-Pierre Kruth, Heverlee (BE); Bart Nuttin, Rotselaar (BE)

(73) Assignees: K.U.Leuven Research & Development, Leuven (BE); IMEC, Leuven (BE)

( * ) Notice: Subject to any disclaimer, the term of this patent is extended or adjusted under 35 U.S.C. 154(b) by 555 days.

(21) Appl. No.: 11/994,374

(22) PCT Filed: Jul. 3, 2006

(86) PCT No.: PCT/BE2006/000077
§ 371 (c)(1),
(2), (4) Date: Dec. 31, 2007

(87) PCT Pub. No.: WO2007/003019
PCT Pub. Date: Jan. 11, 2007

(65) Prior Publication Data
US 2008/0208268 A1 Aug. 28, 2008

(30) Foreign Application Priority Data

Jul. 1, 2005 (GB) .................................. 0513460.6
Jul. 5, 2005 (GB) .................................. 0513684.1

(51) Int. Cl.
*A61N 1/18* (2006.01)
(52) U.S. Cl. .......................................................... 607/2
(58) Field of Classification Search .............. 607/53–55, 607/152
See application file for complete search history.

(56) References Cited

U.S. PATENT DOCUMENTS

| 5,262,945 | A | 11/1993 | DeCarli et al. |
| 6,176,874 | B1 | 1/2001 | Vacanti et al. |
| 7,369,900 | B2 * | 5/2008 | Zdravkovic .................. 607/118 |
| 2002/0187350 | A1 | 12/2002 | Saccomanno et al. |
| 2003/0043957 | A1 | 3/2003 | Pelc |
| 2003/0134505 | A1 | 7/2003 | Dalton et al. |
| 2003/0158588 | A1 * | 8/2003 | Rizzo et al. ..................... 607/54 |
| 2004/0036398 | A1 | 2/2004 | Jin |
| 2005/0085719 | A1 | 4/2005 | Franklin et al. |

FOREIGN PATENT DOCUMENTS

WO WO 00/12607 3/2000
WO WO 96/40002 12/2006

OTHER PUBLICATIONS

International Search Report for PCT/BE2006/000077 Mailed Jan. 3, 2007.
Written Opinion of the International Searching Authority for PCT/BE2006/000077 Mailed Jan. 3, 2007.
International Preliminary Report on Patentability for PCT/BE2006/000077 Mailed Aug. 22, 2007.
Adams et al., "Development of Flexible Arrays for In Vivo Neuronal Recording and Stimulation," *Nucl. Instrum. Methods Phys. Res.* 546:154-159 (2005).

* cited by examiner

*Primary Examiner* — Scott M Getzow
*Assistant Examiner* — Amanda Patton
(74) *Attorney, Agent, or Firm* — Clark & Elbing LLP

(57) ABSTRACT

The present invention relates generally to a method and device of partial or complete functional restoration of the damaged nervous system by bridging a cavity in the central or peripheral nervous tissue and, more particularly to a system and method for repairing the nerve signal transduction by bridging of the cavity with microelectrode elements more particular microelectrodes for stimulation and microelectrodes for recording.

12 Claims, 34 Drawing Sheets a      b      c

40

Flexible electronics = electronics on a foil

U.S. 7,991,465 B2

MEANS FOR FUNCTIONAL RESTORATION OF A DAMAGED NERVOUS SYSTEM

CROSS-REFERENCE TO RELATED APPLICATIONS

This application is the U.S. National Stage of International Application No. PCT/BE2006/000077, filed Jul. 3, 2006, which claims the benefit of Great Britain Application Serial No. GB 0513460.6, filed Jul. 1, 2005, and Great Britain Application Serial No. GB 0513684.1, filed Jul. 5, 2005.

FIELD OF THE INVENTION

The present invention relates generally to a method and device suitable for partial or complete functional restoration of a damaged nervous system, e.g. in a human patient. The damage may be a cavity in the central or peripheral nervous tissue. The present invention also relates more particularly to a system and method suitable for repairing the nerve signal transduction, e.g. in a cavity. The present invention also relates to microelectrode elements more particularly microelectrodes for stimulation and microelectrodes for recording. The present invention is particularly suitable for restoring the interconnectivity between a first excitable cell and a remote second excitable cells, the interconnectivity of which has been interrupted by a cavity (for instance a stable tissue lesion) and for electrical stimulation of the first remote excitable cells proportional to the activity of the second remote excitable cells.

TECHNICAL BACKGROUND

Lesions of the central nervous system are a particular indication of treatment for the use of the present invention. Brain lesions and spinal cord lesions can induce minor or major morbidity. Some of the possible causes of those lesions are trauma (road traffic accidents, falls, fights, surgical interventions in the central nervous system and there exist many other examples of lesions due to trauma), spontaneous haemorrhages (intracerebral haematoma, intramedullary bleeding, cerebellar and brainstem bleeding, haemorrhage after stroke, etc. . . . ), stroke, tumours and infections once they have been partially or completely treated or have healed spontaneously, and perinatal lesions which are usually a cause of cerebral palsy.

The central nervous system consists of the brain, the cerebellum, the brainstem and the spinal cord. The lesions of the central nervous system we want to address in this invention are lesions which are relatively stable in time. This means that the present invention does not address acute infections, growing tumours, recent haemorrhages, etc. Examples of stable lesions are cavities in the nervous system, for instance of the group consisting of central nervous system (CNS) cavities after trauma once the acute phase has resolved, i.e. some weeks or months after the primary injury; CNS cavities after resorption of an intracerebral haemorrhage; CNS cavities after stabilisation of the size of the ventricles and of the circulation of the cerebrospinal fluid; CNS cavities after partial or complete healing of a tumour or infection by any means (surgical resection, chemotherapy, radiation therapy, radiosurgery or stereotactic radiotherapy, immunotherapy); CNS cavities due to perinatal lesions which cause cerebral palsy and which are by definition stable and CNS cavities due to agenesis of a certain part of the central nervous system. This list is not exhaustive and does not preclude the many other examples which can be thought of in the field of lesions of the central nervous system.

An example of brain lesions suitable for the treatment of present invention is demonstrated for instance in FIG. 1. FIGS. 1 $a$, $b$ and $c$ show a stable intracerebral lesion due to a brake of a bicycle which entered the brain after a fall several years before this scan (T1-weighted magnetic resonance imaging) was taken. The patient has dyskinesia (abnormal movements) after this kind of injury. FIG. 1 $d$ is a computerized tomography scan showing a lesion in the caudate nucleus, FIG. 1 $e$ shows a lesion in the globus pallidus, FIG. 1 $f$ in the thalamus.

Another example of brain lesion that can be treated by present invention is shown in FIG. 2. FIG. 2 $a$. shows large brain lesion in both hemispheres, and the cavity, which is filled with fluid, is easily accessible from the outside by a trepanation (operation with opening of a reasonable part of the skull). FIG. 2 $b$. shows large brain lesion in one hemisphere, and the cavity, which is filled with fluid is easily accessible from the outside by a trepanation and FIG. 2 $c$ shows large lesion (hypo-intense on T1-weighted magnetic resonance imaging or dark) in the spinal cord (grey), which causes both sensory and motor loss below the lesion, and both urinary and faecal incontinence.

Up to the date of present invention there was a clear need in the art to restore the nervous system functions, that have been lost by the occurrence of the lesions presented above.

Degenerative disorders of the central nervous system can also be an indication of treatment for the use of this invention.

Thus, there is a clear need in the art for treating nervous system disorders caused by lesions or cavities in said nervous system or for restoring functions of the nervous system that have been disabled by the lesions or cavities. The present invention provides such solution to this problem by bridging of the cavity with microelectrode elements more particular with microelectrodes for stimulation or microelectrodes for recording by repairing the nerve signal transduction. The system of present invention is particularly suitable for lesions which are relatively stable in time.

SUMMARY OF THE INVENTION

The present invention relates generally to a method and device of partial or complete functional restoration of the damaged nervous system by bridging a cavity in a tissue of excitable cells e.g. a cavity in the central or peripheral nervous tissue and, more particularly to a system and method for repairing the nerve signal transduction by bridging of the cavity with microelectrode elements more particularly microelectrodes for stimulation and microelectrodes for recording. The bridging device is particularly suitable restoring the interconnectivity between a first excitable cell and a remote second excitable cells of which has been interrupted by a cavity (for instance a stable tissue lesion) and for electrical stimulation of the first remote excitable cells proportional to the activity of the second remote excitable cells. Accordingly, the present invention is particularly suitable for bridging communication of electric stimuli between interrupted or remote excitable cells.

The present invention concerns a bridging device capable of recording of the activity and stimulation of excitable cells for bridging the electrical signal from a first excitable cell to a second remote excitable cell. The first and second cells can be located within one patient, e.g. within the brain of one person. The bridging device of present invention comprises a substrate and a die on top of the substrate, the die comprising an array of stimulation/recording sites having at least one stimulation means and at least one recording means or comprising an array of sites of recording and/or sites of stimulation. The substrate comprising the die is or a foldable foil with the dimension and shape being customised for fitting again the internal wall of a target cavity, or it is device of which the parts are customised to fit in the target cavity in such way the array of recording and/or stimulation sites when put in position make contact with excitable cell in the vicinity of the border of the target cavity, e.g. the brain of a patient in case of a neuro-bridging device (20) for use in brain lesion bridging.

It is an object of the present invention to provide a bridging device which can deliver stimulation pulses and perform measurements in three dimensions to the edges of a cavity or to the tissues surrounding the vicinity of the edges of the cavity as well as a method of manufacturing and using the same.

It is yet a further object of the present invention to provide a bridging device comprising sensing devices which enable high to low impedance conversion and thus enhance the signal to noise ratio of chronic recordings.

The above objectives are accomplished by a method and device according to the present invention.

An aspect, the present invention is to provide a bridging device for electrical stimulation and recording of activity of excitable cells present in tissue surrounding a cavity in which the array of microelectronic pixels of the bridging device is fitted. For example, the bridging device may be a neuro-bridging device for electrically stimulating neurons present in a brain tissue surrounding a brain lesion and for recording the activity of the neurons in the vicinity of the edges of a cavity that interrupts their interconnectivity. The bridging device according to this aspect of the invention comprises an array of pixels, wherein each pixel comprises at least one stimulation means and at least one recording means or wherein there are zones of pixels comprising stimulating means and zones of pixels comprising recording means.

With recording means is meant means that can be used for measuring, indicating, reading, sensing . . . activity of excitable cells present in a tissue to be examined or treated, in the example given brain tissue, although not limited thereto.

In the bridging device according to the first aspect of the invention, stimulation and recording means can be positioned at a same site, forming a "stimulation/recording-site" or they can be positioned in different zones forming stimulation sites and recording sites.

Furthermore, because an array of stimulation/recording sites and/or sites of recording and/or sites of stimulation is present, it is possible to stimulate excitable cells and record activity of the stimulated excitable cells in at least two directions.

In embodiments of the invention the array of pixels may be located on a die. The die may, for example, be a semiconductor die, such as e.g. a silicon die. In other embodiments, however, the die may be a GaAs die or a SOI (silicon on insulator) die.

According to embodiments of the invention, the die may be positioned on a substrate. The substrate preferably is from biocompatible material, and may for example comprise one of parylene C, parylene N, polyimide, polysiloxane rubber, teflon, a noble metal, titanium, an oxide, $Si_3N_4$ or a biocompatible epoxy. The substrate may be shaped so as to enable, when introduced into tissue of a patient, 3D stimulation of excitable cells present in the tissue and 3D measurement of activity of the excited cells in the tissue. The tissue may, for example, be nervous, cardiac or muscular tissue.

According to embodiments of the invention, the substrate may have a first area and the die may have a second area, wherein the first area is bigger than the second area. The first area may define a shaft of the bridging device and the second area may define an active part of the bridging device.

According to embodiments of the invention, the bridging device may have customised shape in accordance with the 3D structure and dimensions a tissue or organ cavity of an organism. An advantage of such is that the recording and stimulating pixel array can exactly fits into a tissue or organ cavity of a subject such as a mammal and make direct contact with the excitable cells in the vicinity of the edges of that cavity.

In embodiments according to this aspect of the invention, the device may furthermore comprise a biocompatible insulating coating for protection of the probe against corrosion of contacts present on the substrate and on the die.

In a specific example according to the first aspect of the invention, the bridging device may be a neuro-bridging device for brain lesion bridging (BLB). The neuro-bridging device may comprise:
 a substrate having a top surface, and
 a die positioned on the top surface of the substrate, the die comprising an array of stimulation/recording sites,
wherein each stimulation/recording site comprises at least one stimulation means and at least one recording means.

In a second aspect of the present invention, a method is provided for the manufacturing of a bridging device according to the first aspect of the invention. The method comprises providing an array of pixels, each pixel comprising at least one stimulation means and/or at least one recording means. Such array pixels is obtainable by deposition on a die.

With recording means is meant means that can be used for measuring, indicating, reading, . . . activity of excitable cells present in a tissue to be examined or treated, for example brain tissue.

The method according to the second embodiment of the invention provides a bridging device wherein stimulation and recording means are positioned at a same site, forming a "stimulation/recording-site". Furthermore, because an array of stimulation/recording sites and/or sites of recording and/or sites of stimulation is present, it is possible to stimulate excitable cells and record activity of excited cells in at least two directions.

According to embodiments of the invention the method may furthermore comprise providing the array of pixels on a die.

In further embodiments, the method may furthermore comprise thinning the die comprising the array of pixels. This step may be required in particular when the die is formed of a thick substrate such as Si or GaAs. However, when the die is formed of SOI (silicon on insulator) this step may be omitted because the SOI die may be made thin enough before the start of the manufacturing of the bridging device.

The method according to the second embodiment of the invention may furthermore comprise bonding the die comprising the array of pixels onto a substrate.

According to embodiments of the second aspect of the invention, the method may furthermore comprise shaping the substrate on a customised way involving 3D imaging of the to be implanted target cavity and rapid prototyping of the mold in accordance with the 3D structure and dimensions of the target cavity and so as to enable the bridging device, when introduced into the cavity of an organism for instance a mammalian patient, to perform 3D stimulation of excitable cells present in the tissue surrounding the edges of the cavity and 3D measurement of activity of the excitable cells in the tissue surrounding the vicinity of the edges of the cavity. In some embodiments, shaping the substrate may comprise folding or bending the substrate and eventually shrinking over a mold with dimension approaching the target cavity.

In the method according to embodiments of the second aspect of the invention, the die may be bonded onto the substrate by means of wire bonding. In other embodiments, the die may be bonded onto the substrate by means of the flip-chip technique.

According to embodiments of the second aspect of the invention, the method may furthermore comprise providing a biocompatible insulating coating for protection against corrosion of contacts present on the substrate and on the die.

In a specific example of the second aspect of the invention, a method is provided for the manufacturing of a neuro-bridging device for performing brain lesion bridging. The method may comprise:

providing a substrate having a top surface, providing a die comprising an array of stimulation/recording sites or stimulation sites or recording sites, each of such site comprising at least one stimulation means and at least one recording means, thinning the die comprising an array of sites of stimulation and or recording, bonding the die comprising an array of stimulation/recording sites or stimulation sites or recording sites on the top surface of the substrate, and folding the substrate for instance on an internal or external mold with the dimension and 3D shape of a target tissue lesion thus forming a device expandable to a customised shape corresponding to the shape of the borders of the target tissue lesion having an outer side, wherein the folding of the substrate is such that when in position in the cavity the stimulation/recording sites and/or sites of recording and/or sites of stimulation fit to the surrounding border of the cavity.

In a third aspect of the invention, a method is provided for determining a stimulation pattern for application to excitable cells in a tissue using the probe-device according to the invention. The method comprises:

recording electrical activity of excited cells, comparing the recorded electrical activity to predetermined activity values of the excited cells, and from the comparison, determining the stimulation pattern.

The invention also includes a computer program product which, when executed on a processing device, executes the method according to the third aspect of the invention, and a machine readable data storage device storing the computer program product according to the invention.

In a fourth aspect, the present invention provides a device for determining a stimulation pattern for application to excitable cells in a tissue by means of a bridging device according to the first embodiment of the present invention. The device comprises:

a bridging device according to the first embodiment of the present invention for recording electrical activity of excited cells and generating corresponding activity signals, processing means for comparing the generated activity signals with pre-determined activity signals for the excited cells, and stimulation pattern determining means for generating, from said comparison, stimulation pattern parameters of the stimulation pattern. The stimulation pattern parameters may comprise frequency and/or amplitude and/or pulse duration. Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings

DEFINITIONS

An organism for the meaning of present application is a an individual form of life, a body made up of organs, organelles, or other parts that work together to carry on the various processes of life, such as a plant or animal; while an organ is in the meaning of a differentiated part of an organism, such as an eye, heart, brain, liver or leaf, that performs a specific function.

Excitable cells are cells that respond actively to an electric stimulus or can propagate action potential or that can be stimulated to create a tiny electric current, for instance neurons, muscle cells (for instance cardiomyocytes) and beta-cell from the islets of Langerhans of the pancreas, secretory pituitary cells, cells in the adrenal medulla. Excitable cells in tissues can be modulated by electric fields

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 5.b. provides a drawing on the use of cannula and stylet. The large stylet with a blunt tip is withdrawn from the cannula. The cannula wall has been marked by the number code 9.

FIG. 5.c. The folded balloon or balloon-like structure (which is constructed as explained in illustrated embodiments of the invention, Examples) is inserted into the cannula. Different stylets (10) have been fixed to the inside of the balloon or balloon-like structure (5), just at extremities of the balloon or balloon-like structure. This can be produced based on the 3D-structure of the lesion cavity as visualized by imaging techniques. The balloon or balloon-like structure and stylets (10) are surrounded by a biocompatible tube (14) with good mechanical stability, which fits just inside the cannula (9). The base of this tube is fixed to the balloon or balloon-like structure. The top of this tube has screw thread, directed to the inner lumen of the cannula, in order to be able to close the balloon or balloon-like structure later-on. On the outside of the top of the tube are some irregular structures (e.g. 2 or more pins) which can immobilize the tube into bone cement which will be applied later-on in the burr hole. The stylets are about straight as long as they remain in the stiff tube. However, once they will be pushed down, they will take on a posture as planned before the construction of the device after having analyzed the data of the 3D imaging of the lesion cavity. The correct position of each balloon or balloon-like structure extremity is important. This is for instance obtainable by marking. Marking every stylet and also the tube will enable the surgeon to orient the device correctly. One of the possible strategies can be to mark the anterior direction on both the grip of the stylet and the top of the screw thread, although it is evident that there are plenty of other possible ways of marking the instruments in order to provide good orientation. The number of the stylets depends upon the number of extremities of the 3D-volume or the dimension of the cavity and can vary between 1 and 20, but the less stylets, the easier the application. Medical biocompatible tubes, balloon or balloon-like structure and stylets for insertion into the human body are well known in the art. Biocompatible tube material with good mechanical stability (e.g. polyurethane,), Teflon®-coated stainless steel stylet and latex balloon or balloon-like structure have been approved for use in humans.

The length of the hard extension of the balloon or balloon-like structure depends upon the distance between the lesion and the skull, and this length can be obtained from the imaging data, just like planning a stereotactic intervention. This procedure is known to stereotactic-neurosurgeons.

Number codes 12=grip of a stylet, optionally with a mark pointing into e.g. anterior direction; 13=a screw thread which can be fixed to hard extensions of the balloon or balloon-like structure. On top of this screw thread can be a mark pointing anteriorly. Laterally can be 2 or more pins to become fixed in the cement; 14=the hard extension of the balloon or balloon-like structure, which remains in place after insertion, and is preferably as long as the distance between burr hole and balloon or balloon-like structure. It can be longer than depicted in the figure. 10=the stylet; 5=the balloon or balloon-like structure, which resembles the 3D-structure of the lesion cavity; 9=the cannula wall. This cannula is removable after insertion of the balloon or balloon-like structure. It can be longer than depicted in the figure.

Figure 5:
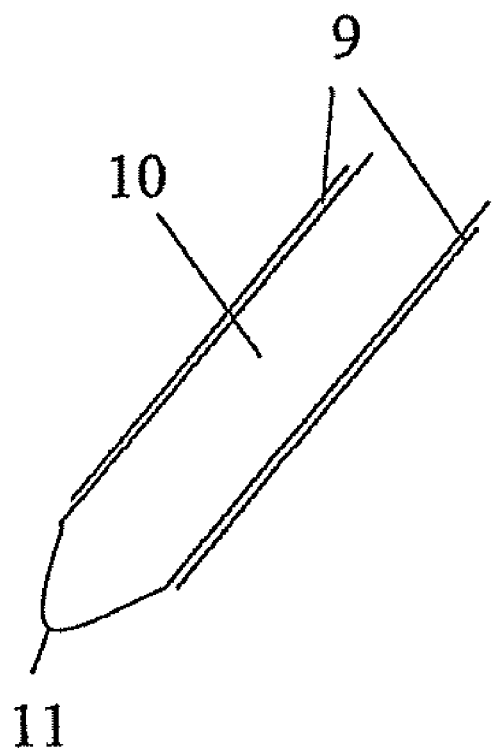
FIG. 5.a. provides a drawing on the use of cannula and stylet. After having made a burr hole, a cannula with large stylet, which preferably fills the entire volume of the cannula, with a blunt tip, is inserted into the brain, using a classical stereotactic approach. This means that the surgeon knows exactly where in space this cannula is situated. Because the current positioning and imaging systems enable the surgeon to know exactly where the 3D-lesion cavity is situated, the surgeon will also know the position of the cannula relative to the lesion cavity. The cannula wall has been marked by the number code 9, the (insertion) stylet by 10 and the blunt tip by 11.
Figure 5:
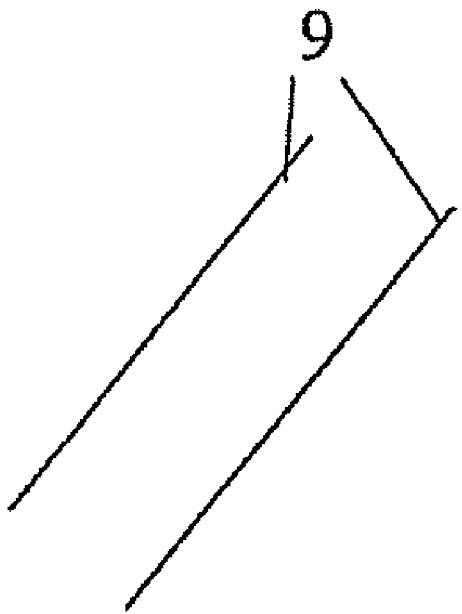
Figure 5:
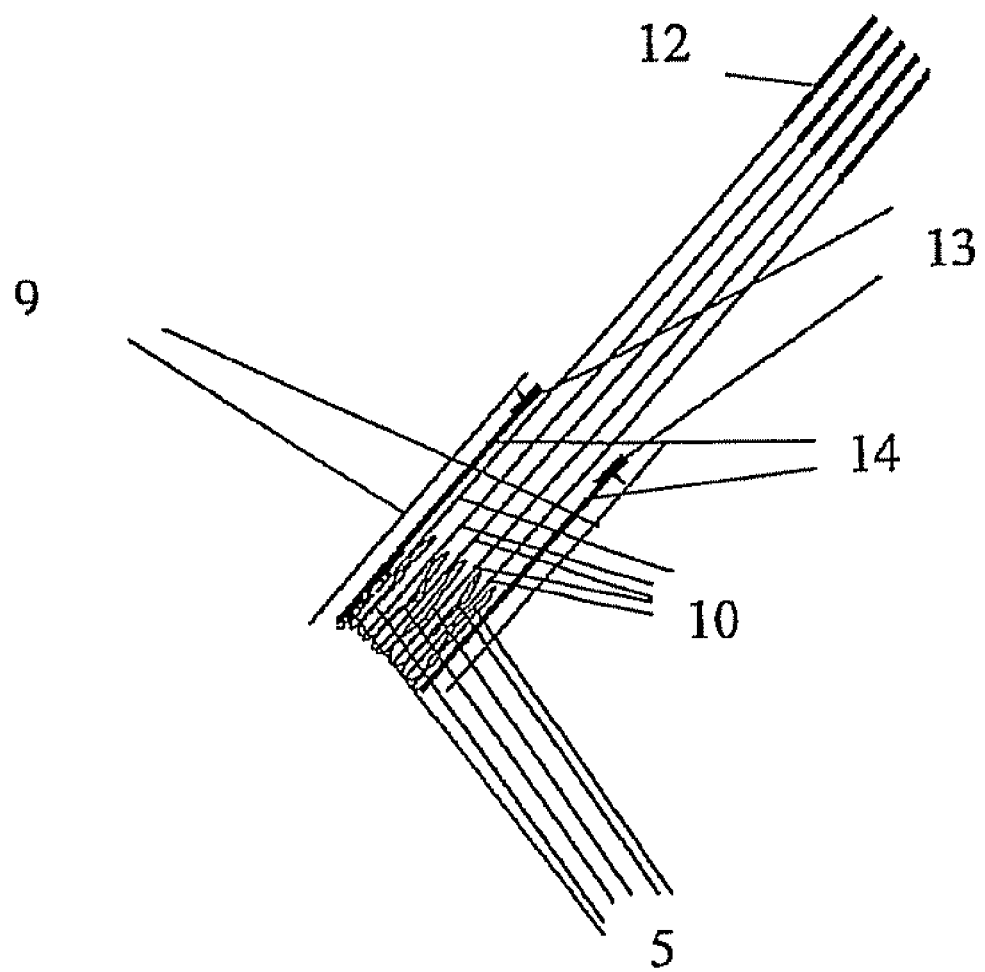
Figure 5:
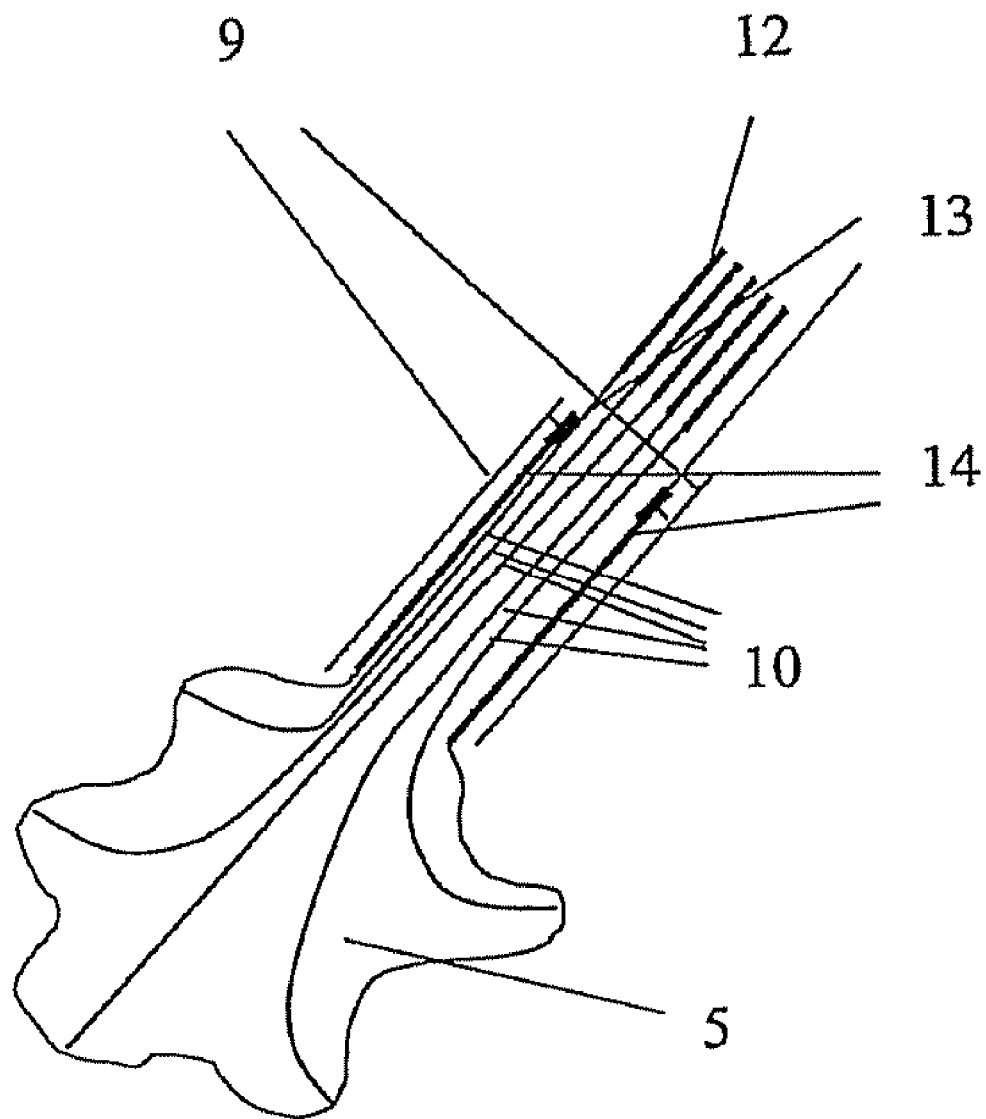
Figure 5:
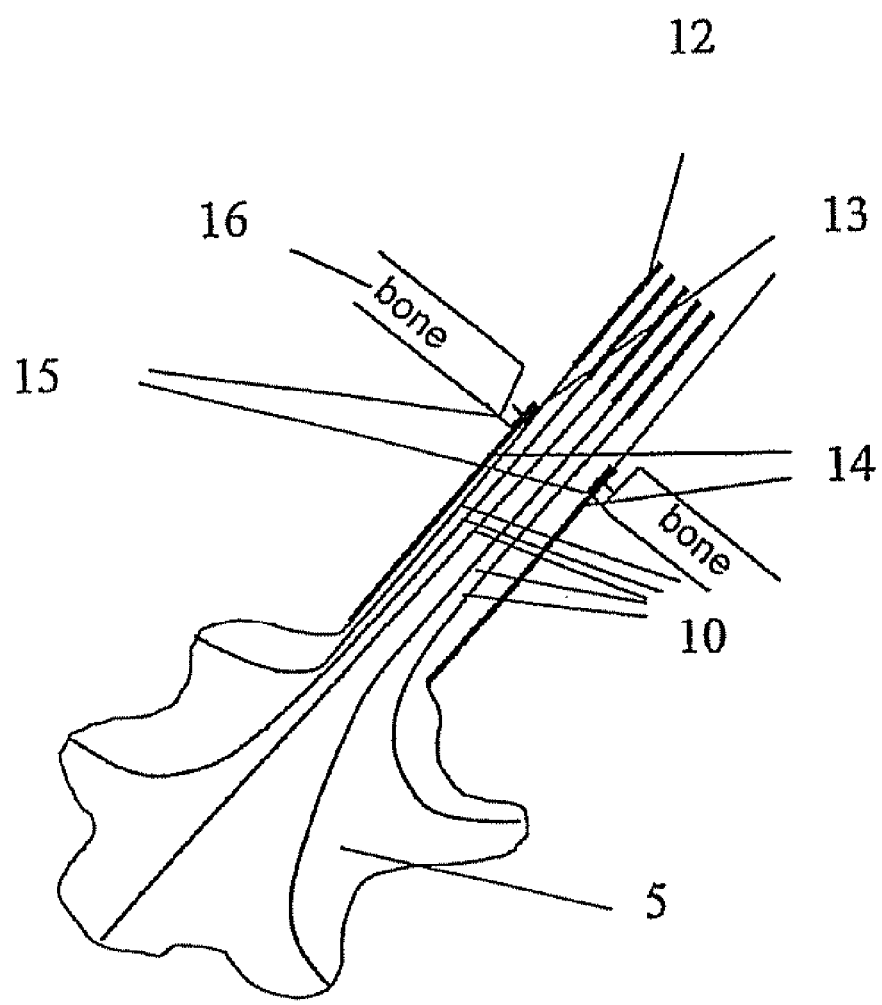
Figure 5:
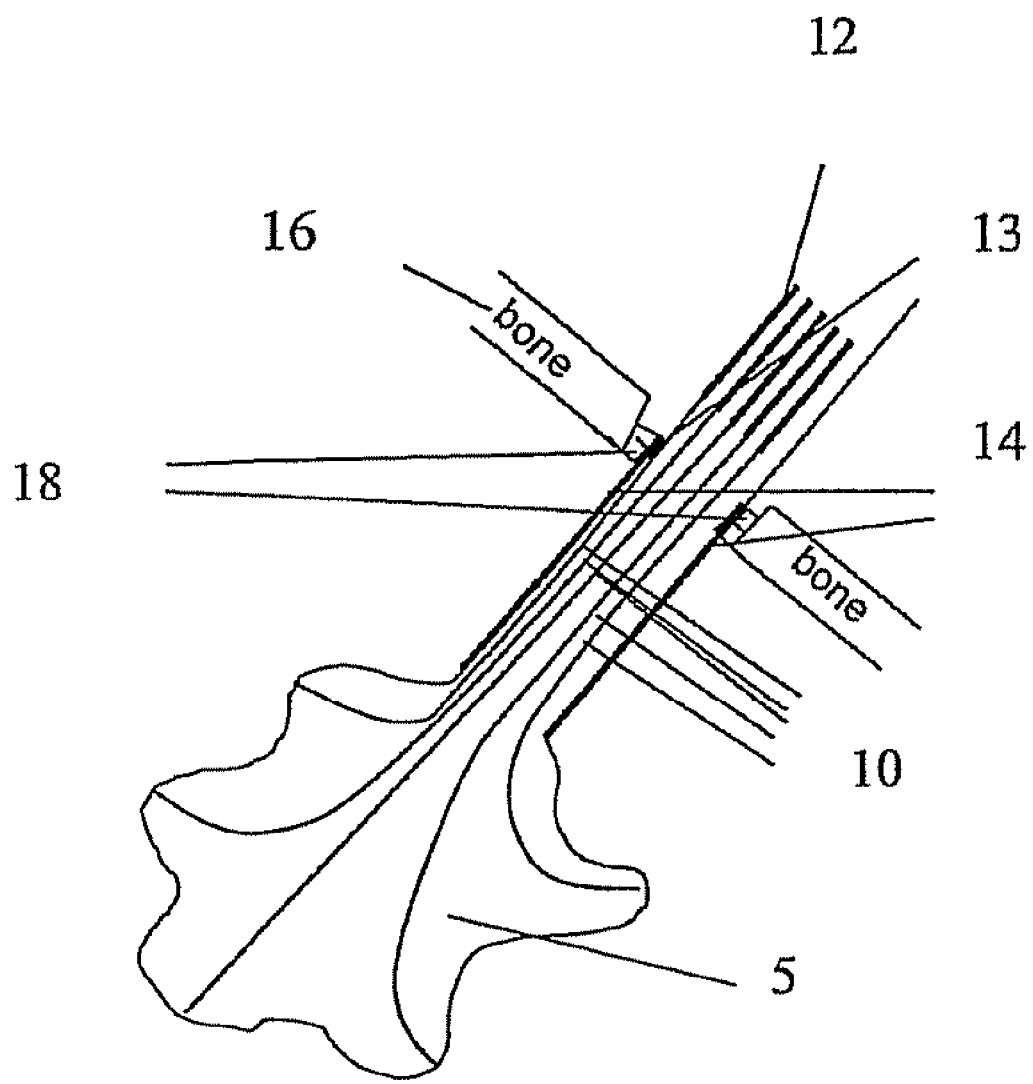
Figure 5:
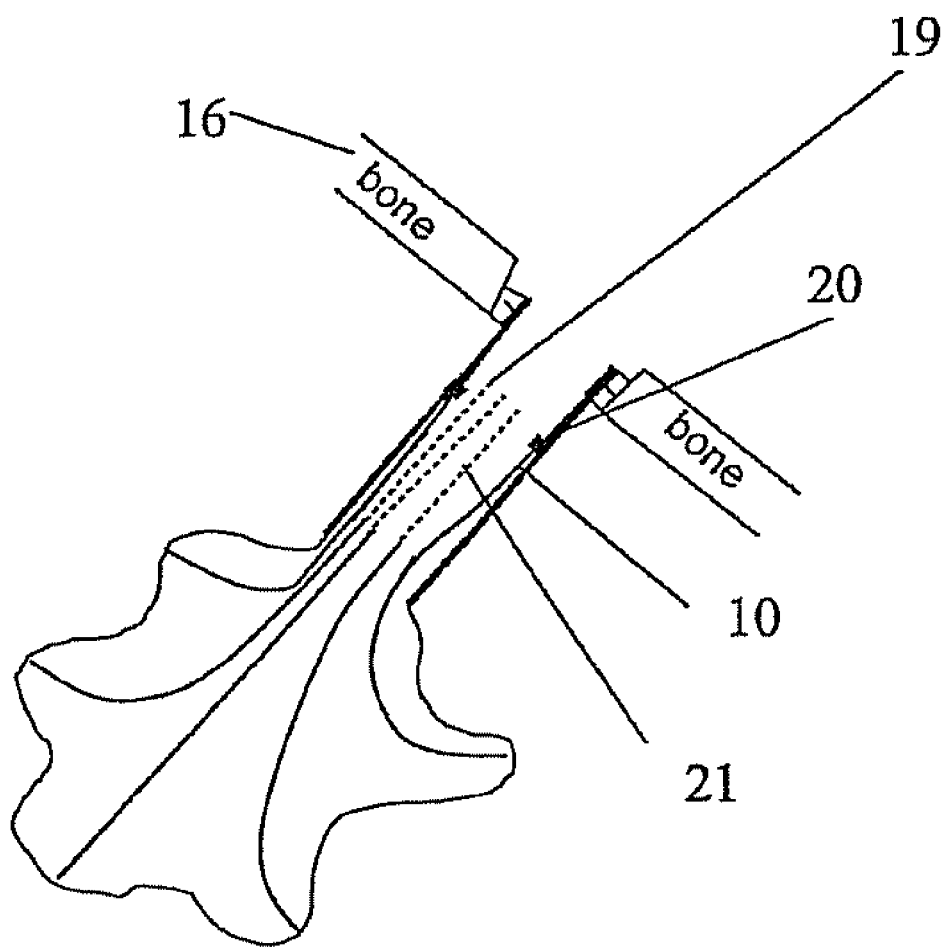
Figure 5:
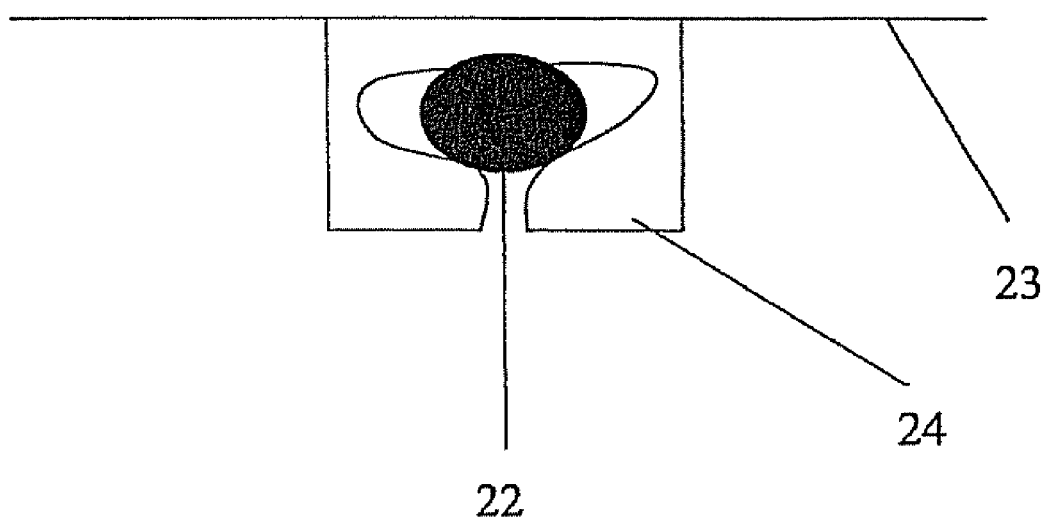
Figure 5:
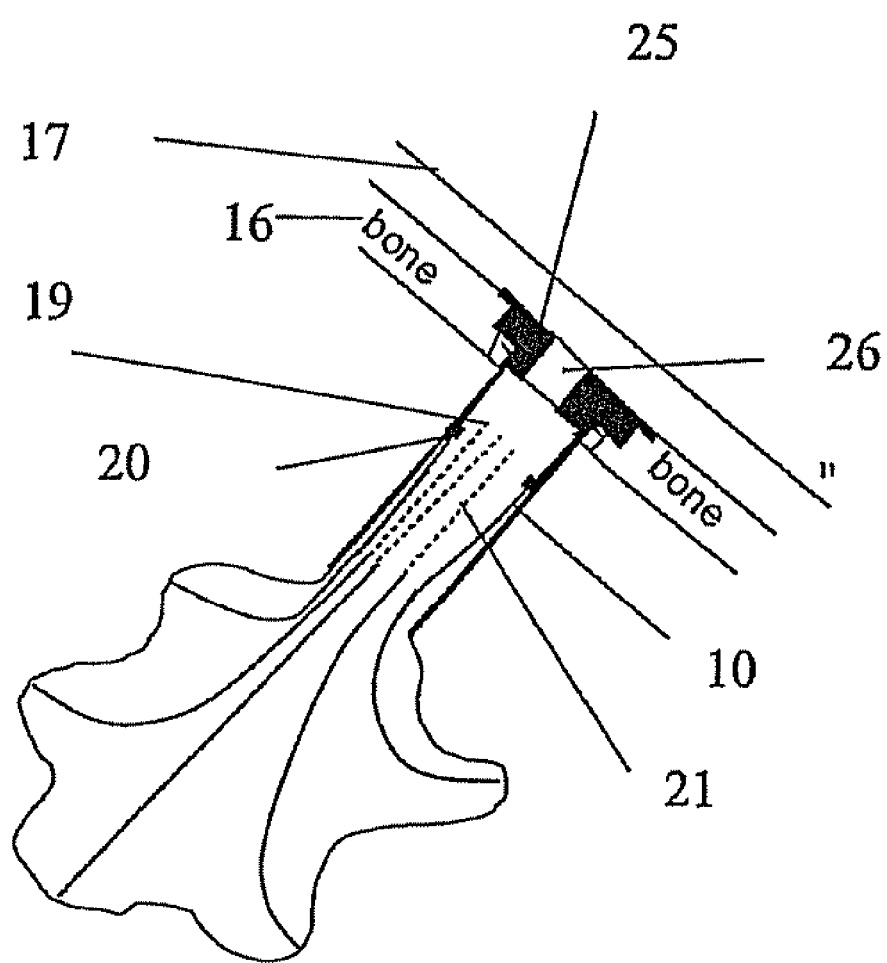

FIG. 5.d. shows the stylets in a position of having been pushed down. The number codes in this figure are: 12=the grip of a stylet; 13=the screw thread; 14=the hard extension of balloon or balloon-like structure or the hard biocompatible tube. This can remain in place after insertion, and is preferably as long as the distance between burr hole and balloon or balloon-like structure; 5=the balloon or balloon-like structure, which can resemble the 3D-structure of the lesion cavity if in expanded position and carries the electrical stimulation and electrical recording sites at its surface and 9=the cannula wall. This can be removed after insertion of the balloon or balloon-like structure, but does not have to be. It can be shorter (which is not preferred) than depicted in FIG. 5, or longer, so it fits into a guide of the stereotactic frame (preferred situation).

FIG. 5.e. shows the condition of the assembly after the cannula has been removed and some biocompatible material (15), preferably scaffolding material and most preferably absorbable haemostatic scaffolding material such as the oxidized celluloses (e.g. Oxycell) or collagens (15) has been (but does not have to be) placed between the hard extension of the balloon or balloon-like structure (14) and the bone (16) to prevent later-on the bone cement from entering below the dura mater. The number codes in this figure mean 12=grip of a stylet, which preferably has a mark in the direction of the bent tip; 13=screw thread, preferably fixed to hard extension of the balloon or balloon-like structure; 14=the hard extension of the balloon or balloon-like structure. This can remain in place after insertion and is preferably as long as the distance between burr hole and balloon or balloon-like structure;

5=balloon or balloon-like structure, which preferably resembles the 3D-structure of the lesion cavity; 10=the stylet; 15=the biocompatible material, preferably absorbable haemostatic scaffolding material such as the oxidized cellulose, Oxycell; 16 is the bone surrounding the neuronal system.

FIG. 5.*f*. shows the assembly after bone cement (18) is added on top of the scaffolding material Oxycell (15). The surgeon waits until the bone cement is hard, which usually takes 5 to 10 minutes, but can take longer, depending on which bone cement is used. In order to provide a good fixation of the hard tube to the bone, it is advisable (although not essential, as other forms of the burr hole are possible) to make at least 3 holes in the bone at the base of the burr hole. The number codes in this figure mean 12=the grip of a stylet, which preferably has a mark which enables to know the direction of the bent tip; 13=the screw thread. This can be fixed to the hard extension of the balloon or balloon-like structure; 14=the hard extension of the balloon or balloon-like structure, this remains in place after insertion, and is preferably as long as the distance between burr hole and balloon or balloon-like structure; 10=stylet, which can comprise cm/mm marks (or marks with distances which can be related to cm/mm marks); 5=balloon or balloon-like structure, which preferably resembles the 3D-structure of the lesion cavity; 18=bone cement and 16=the bone surrounding the neuronal system.

FIG. 5.*g*. demonstrates the assembly after the stylets (10) have been pushed to the side into fixation points for the stylets (20), which are located at the inside of the hard tube. During this procedure the surgeon watches that the stylet (10) is only fixed once it is located at the correct depth, which is planned presurgically and which can be read from millimetre and centimetre markings onto the stylets. Once the stylets are fixed into the fixation points, the rest part of the stylets above of the fixation point can be cut, either by breaking them, or by cutting them with a cutting instrument. The number codes in this figure mean 19=a display of the level where the styles are cut. This level can be any level inside the tube (14); 20=fixation point for stylet; 10=stylet, preferably with cm/mm marks, which is fixed into fixation points for stylet (20); 21=the stylets, which are preferably fixed to the wall of the balloon or balloon-like structure at fixation points in front and behind this page and 16 is the bone surrounding the nervous system.

FIG. 5.*h*. Example of a fixation point for a stylet. Alternative types of fixation points are available on the market or can yet be designed. The number codes in this figure mean 23=the balloon or balloon-like structure wall or the tube wall; 24=semi)flexible plastic, which opens upon pressure and immediately closes when the stylets fits inside and 22=stylet which has been pushed in the fixation point.

FIG. 5.*i*. demonstrates the assembly after a screw is tightened onto the screw thread. Thereafter a needle can be inserted to inject fluid. Another needle can evacuate air. The needle can be any needle, but preferably a Hueber needle and the device which enables punctures without leakage of fluid can be made out of the same material as used in a Synchromed pump (Medtronic Inc.) or any similar material. These needles can be part of the assembly of present invention. The screw can be wider than the burr hole and one or more holes can be made laterally (not depicted on the figure). Such holes can be filled with a smaller screw (e.g. a self-tapping screw) in order to secure the major screw to the bone, once it is tightened. The self-tapping screws provide additional fixation of the whole device to the bone. The number codes in this figure mean 25=screw, which perfectly fits the screw thread in a water tight fashion. It also fits the bone contour, which can be drilled accordingly at the start of the operation with drills which have the same dimensions as the screw; 26=devices which enables punctures without leakage of fluid; 10=stylet, preferably with cm/mm marks; 21=stylets, fixed to the wall of the tube at fixation points in front and behind this page; 20=fixation point for stylet; 19=a display of the level where the stylets can be cut; 16=the bone surrounding the nervous system and 17=the skin surrounding the bone.

Figure 6:
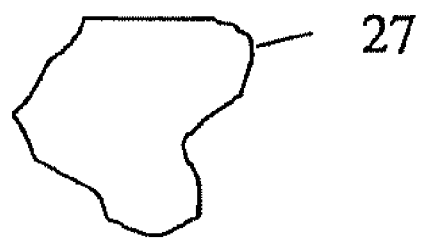
Figure 6:
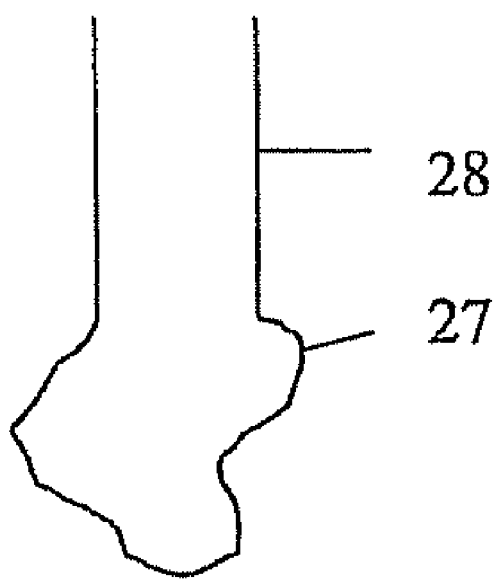
Figure 6:
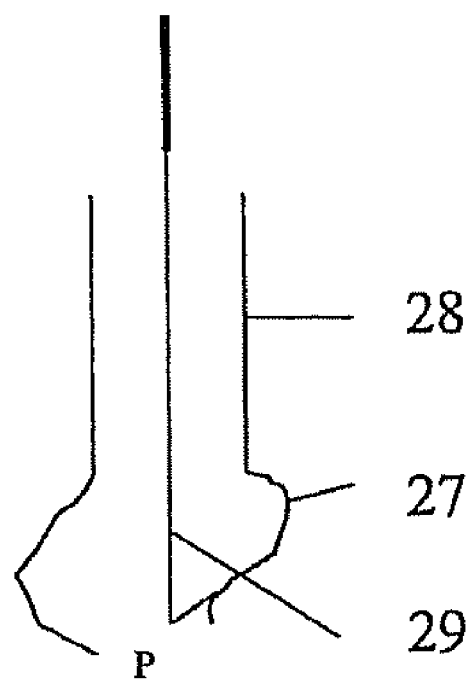
Figure 6:
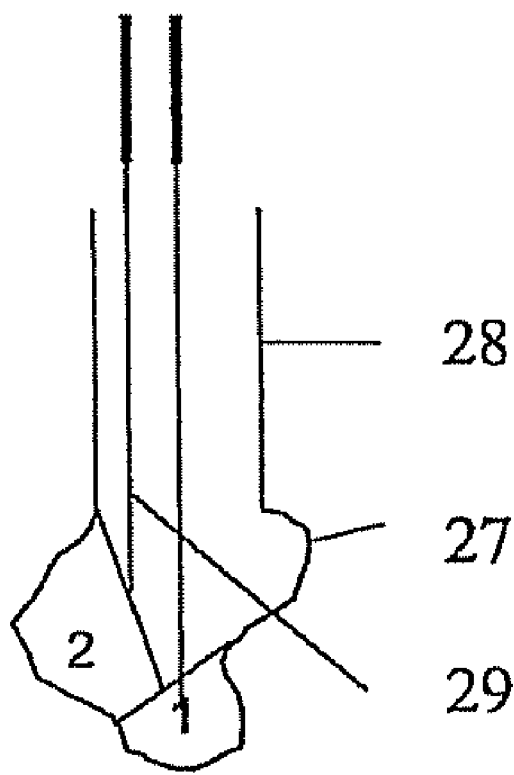
Figure 6:
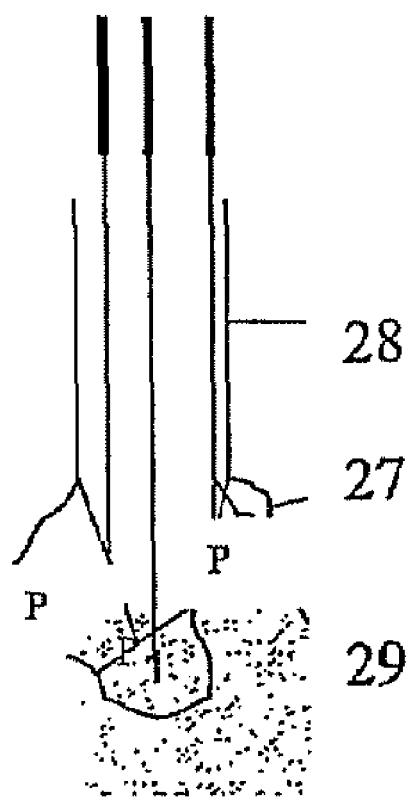
Figure 6:
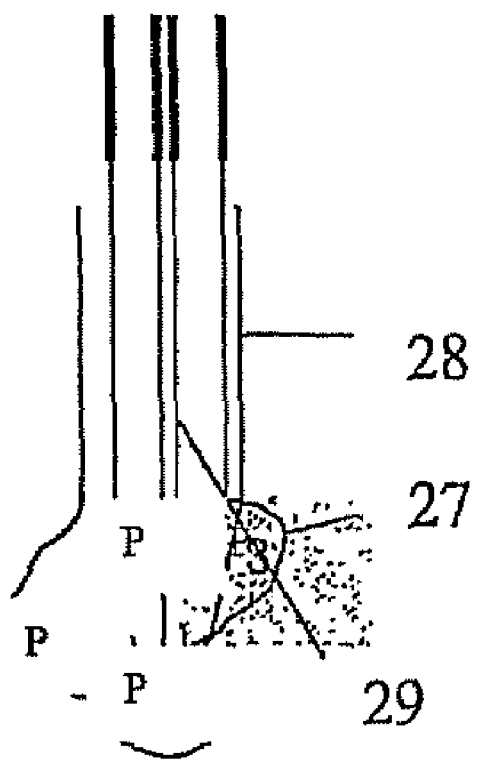
Figure 6:
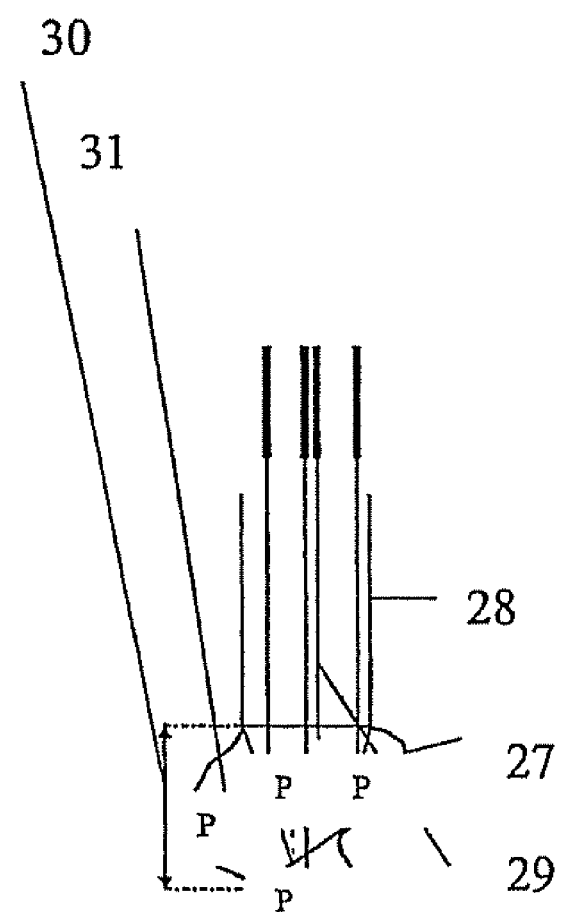

FIG. 6 *a*. is a drawing showing the wall of the lesion cavity (27) in the nervous system.

FIG. 6 *b*. is a drawing showing a cannula or tube (28) which is insertable through a burr hole just like for the insertion of the balloon or balloon-like structure. 27=the lesion wall.

FIG. 6 *c*. is a drawing demonstrating that a Piece 1 (P1) is insertable with the help of an introducer (29). It is possible to move the introducer (29) up and down and also in medial and lateral direction, as long as the introducer stays inside the tube (28). Piece 1 comprises or is covered with some until many thousands of microelectrodes for stimulation and/or recording or with an array of pixels comprising at least electrical stimulation/recording means. The side which does not touch the wall (27) of the lesion cavity is preferably not covered with such microelectrodes, but is the side where all wires can leave piece 1. Inside piece 1 wires can be stored. It is even possible to store a stimulator or many microstimulators in this place.

FIG. 6 *d*. is a drawing demonstrating that Piece 2 (P2) is insertable with the help of a second introducer (2). As is clearly shown in this figure it was only possible to first place Piece 1 (P1) and then Piece 2 (P2), and not the other way around. The umber codes in this figure mean 28=tube; 27=lesion wall and 29=introducer. Similar to Piece 1, Piece 2 comprises or is covered by a microelectrode carrying device.

FIG. 6 *e*. is a drawing that demonstrates that Piece 3 (P3) is insertable. The number codes in this figure mean 28=tube; 27=lesion wall and 29=introducer. Similar to Piece 1 and Piece 2, Piece 3 comprises a microelectrode carrying device.

FIG. 6 *f*. is a drawing that demonstrates that Piece 4 (P4) is insertable. This piece does not cover any microelectrodes, but keeps pieces 1, 2 and 3 in place just by its mechanical presence. This piece can have a structure which is a f111 piece, if microstimulators can all be placed in pieces 1 (P1), 2 (P2) and 3 (P3). However, it is possible that all stimulators do not fit in there. Then wires and stimulators can be placed in piece 4. It is also possible to bring all wires through the tube (which can either be withdrawn or left in place) and place the stimulators in the tube, in the burr hole, somewhere else in the body or even outside the body. In the last case the best is to connect all wires with extension cables which leave the body preferably 10 or 20 cm further away to prevent infection. The number codes in this figure mean 28=tube; 27=lesion wall and 29=introducer.

FIG. 6 *g*. This figure shows what is meant by depth and transverse diameter. The transverse diameter is measured in a plane perpendicular on the tube, whereas the depth is measured in the plane of the tube. The number codes in this figure mean 28=tube; 27=lesion wall and 29=introducer; 30=a display of the depth of P2 and 31=the transverse diameter of P2.

Figure 7:
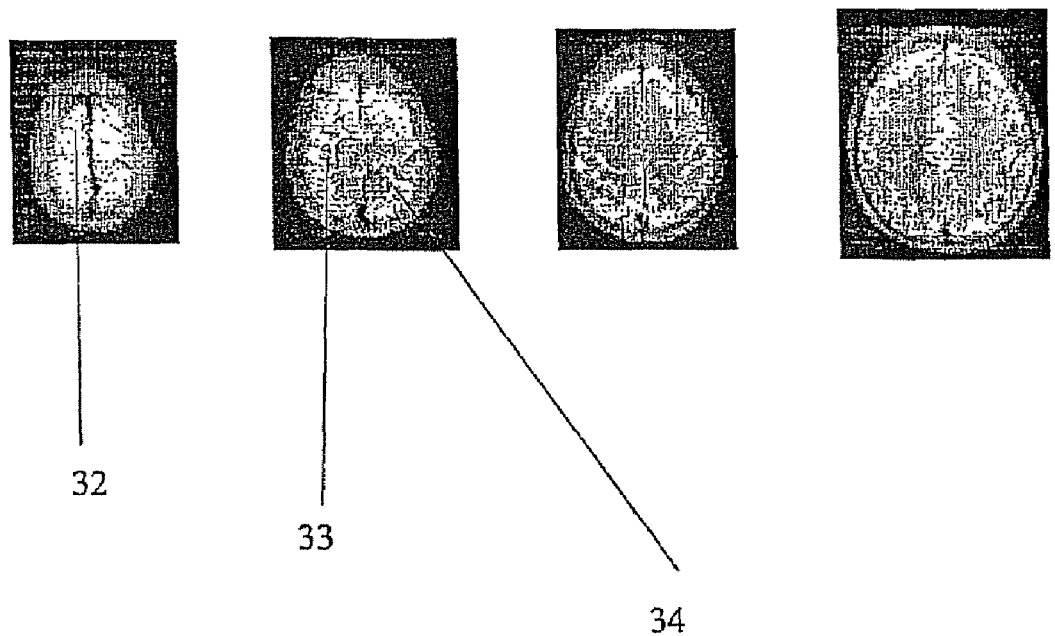
Figure 7:
Figure 7:
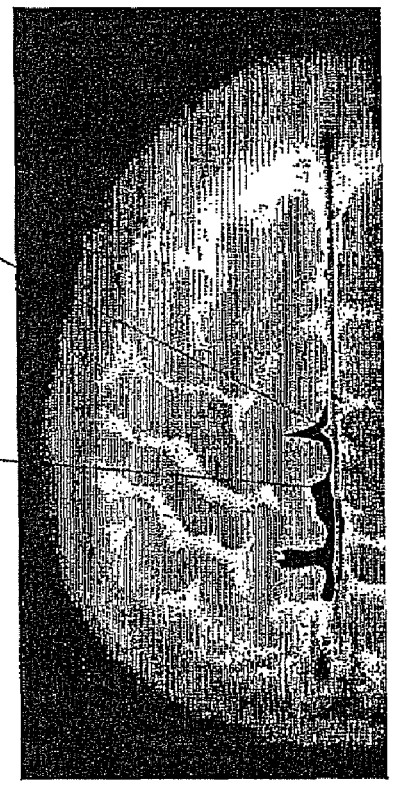
Figure 7:
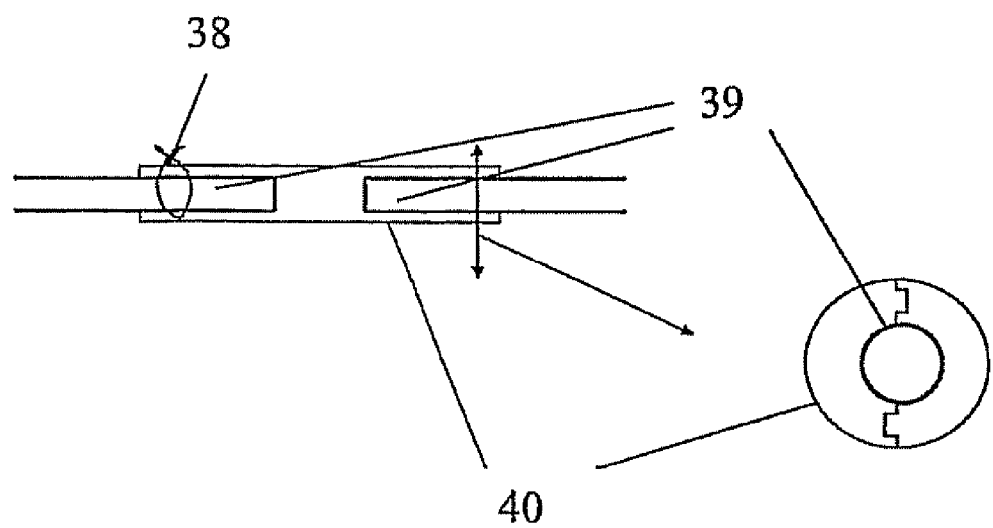
Figure 7:
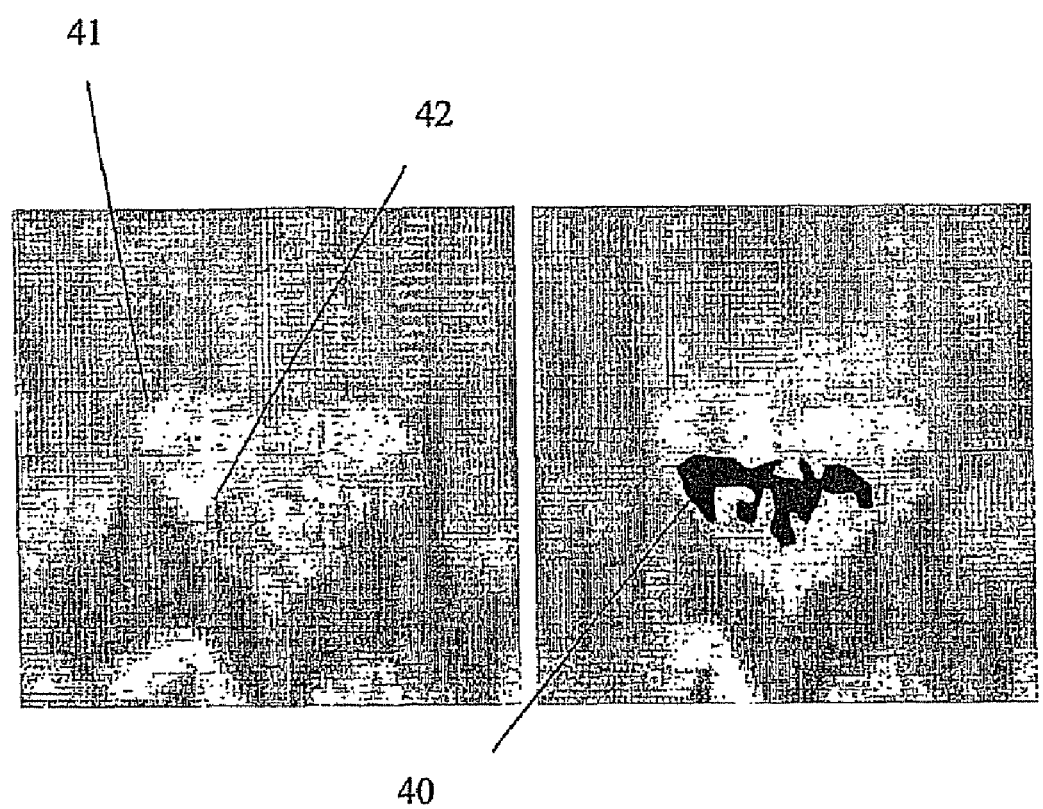
Figure 7:
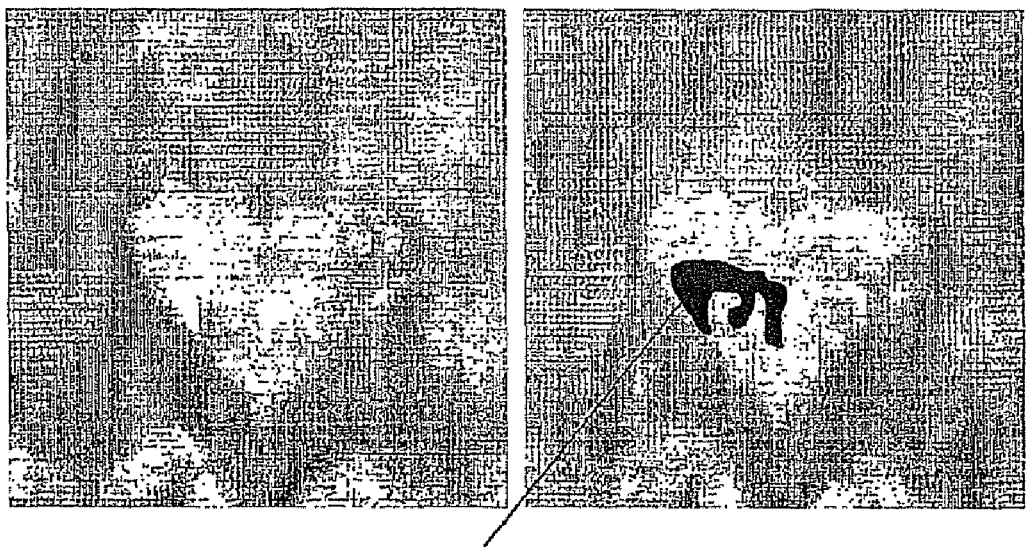
Figure 7:
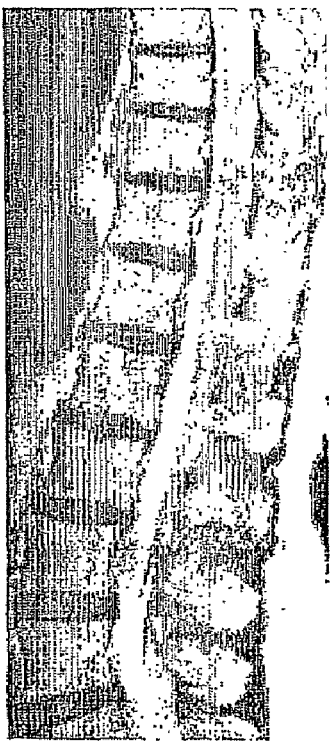
Figure 7:
Figure 7:
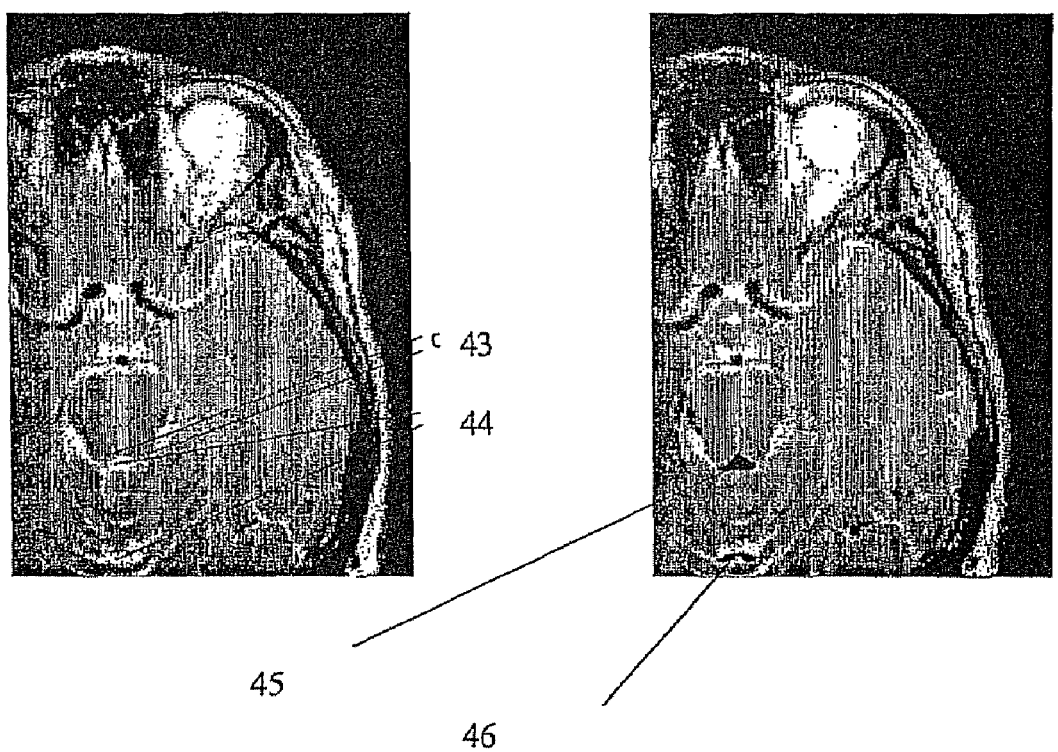

FIG. 7 *a*. Axial T2-weighted MRI slices through the upper part of the brain, showing cortex with the gyri, sulci, cerebrospinal fluid and blood vessels. The number codes in this figure mean 32=blood vessels; 33=cortex (gyrus) and 34=sulcus with cerebrospinal fluid.

FIG. 7 *b*. The black delineated structure is a manual delineation of the sulcus and the space between the falx (which is made of dura mater), avoiding to enter the cortex and the blood vessels. The structure can also be delineated in images of the adjoining brain slices. When the slices are thin (1 or 2 mm thick slices) a 3D-volume can be created. There exist automatic delineation programs on the market as well. Just like the production of the balloon or balloon-like structure or the production of the electrode made of many pieces, a hard or flexible structure with the same 3-D volume as part of the cerebro-spinal fluid space is producible using rapid prototyping techniques for reconstruction of the lesions. After imaging of the lesion by CT scan, MRI, multiplanar reconstruction of MR Images or Angiogram to conduct 3D images of lesion, a rapid prototyping & manufacturing technology can be used to reconstruct the pieces which fit in the lesion cavity. Rapid prototyping & manufacturing technology is available in the art (e.g. Materialise and Medicim NV). On the side of the cortex (or on the outside of the balloon or balloon-like structure or of the electrode made of many pieces) a number (between 2 and many thousands or millions) of microelectrodes for recording and stimulation are placed. There are no microelectrodes at the side of the falx.

Of course a similar device can also be delineated anywhere on the surface of the central or peripheral nervous system, or in superficial or deep sulci (e.g. the lateral sulcus, the Rolandic sulcus, subdurally or subarachnoidally, or even epidurally) and even on and between the folia of the cerebellum or around the brainstem or around the spinal cord or around spinal cord and nerve roots or between the nerve roots of the cauda equina or around an injured peripheral nerve. Examples of those last applications are shown in FIG. 7 C. The number codes in this FIG. 7 b. mean 35=sparing of a blood vessel; 36=custom made electrode and 37=Falx.

FIG. 7 c. displays a peripheral nerve with an injury (in this case a complete transsection, but it can be a partial transsection as well) which is surrounded by the device, which can be made, again based on the 3D-structure as visualized with medical imaging techniques, just as all the devices discussed earlier. The outer part is depicted as a tube, but can be shaped so that it fits the contours of the surrounding muscles, fascia, ligaments, bone, blood vessels etc. with small holes on the side in order to be able to fix it to the surrounding fascia on top of the surrounding muscles. Between 2 and many thousands or millions of microelectrodes for stimulation and recording, both at the level of the proximal and the distal nerve ending are at the edge between the nerve and the device, both at the level of the transsection and at the cut edge. It is likely that many distal axons are dead due to Wallerian degeneration, but there can be axons which are alive and can still conduct a signal upon electrical stimulation. The difference between this device and existing devices is the multitude of contacts with axons and the availability of recording and stimulating electrodes, which are linked to each other with a computer so that a relevant recording can induce a relevant stimulation to bridge the gap interrupting the interconnection of electrical signals between neurons. The same strategy as with the balloon or balloon-like structure can be used (see further: "Practical functioning of the different devices, described in this invention in order to restore function"), and thus, functional bridging of nerves can be achieved. In this way it can be possible to restore motor, sensory and autonomic function. The number codes in this figure mean 38=suture; 39=nerve and 40=device.

FIG. 7 d. displays transverse section of the spinal canal, T2-weighted MR-image. On the right side a device (black on the right-sided image) is drawn, which mimics perfectly part of the cavity or relevant parts of the cavity filled with cerebrospinal fluid (white on the left-sided image). The device can be made of a relatively soft material and is on the outside full with recording and stimulating electrodes. The number codes in this figure mean 41=the edge of spinal canal at the level of the cauda equina, transverse section using T2-weighted MR-images, where white means cerebro-spinal fluid, and grey/black means nerve roots, 42=nerve root of cauda equina and 40 device.

FIG. 7 e. displays a similar image as in FIG. 7 d. The device (40) is smaller. It is clear that the device can be designed such that it covers the damaged nerve roots or those nerve roots which need to be stimulated in order to provide tingling sensations at the site of the chronic neuropathic pain. These devices, covered with stimulating and/or recording electrodes can be connected via a computer with devices implanted around the spinal cord rostral (i.e. more located in the direction of the head) to a spinal cord injury or even in the spinal cord cavity (which was created by the spinal cord injury). In this way motor information will be recorded in the more rostrally implanted electrodes, and stimulation can be done at the level of the more caudal device via the stimulating electrodes (which is implanted in the lesion cavity of the spinal cord, around the more caudally located spinal cord, around certain relevant nerve roots of the cauda equina, at the level of a peripheral nerve or in the muscle itself. For the sensory information the caudal recording electrodes are used and the information is sent via the computer to the stimulating electrodes of the more rostrally placed devices.

FIG. 7 f. displays a sagittal transsection through the spinal canal, T2-weighted MR-images. The device (40) is placed around the cauda equina, also based upon medical imaging. It is in fact the same device as in FIG. 7 c, but there are interactions between microelectrodes (stimulating and recording) at the edges between the nerve roots and the device, and the device has many holes. There should be no sharp edges at the upper and lower border of the device, in order not to damage the nerve roots of the cauda equina. Sometimes it can suffice to bridge only one or some nerve roots. The indication can be to bridge a damaged nerve root, or to perform nerve root stimulation as a treatment for chronic neuropathic pain or to bridge a spinal cord injury as explained above. The outer part of the device does not need to be a circle as depicted in figure FIG. 7 c, but is a 3D-structure, which is based upon medical imaging (especially T2-weighted MRI images), taking care not to compress any nerve roots or other tissues, especially not where the nerve roots are leaving the spinal canal, and the device should be as small as possible, so that it can move together with the nerve roots up and down when the patient is bending forward and backward, so that the microelectrodes remain in contact with the same axons in all positions.

FIG. 7 g. provides an example of a device for recording and stimulation of the (either superior or inferior) colliculus and of the cerebellum. The insertion can be done in a similar way as insertion of the balloon or balloon-like structure or the puzzle device or via the subarachnoid space via an open operation or via classical endoscopic techniques. It should be clear that those are only examples of possibilities. Everywhere at the edge between nervous tissue and other tissue, such a device can be placed. One embodiment of present invention will be placing it there where cerebrospinal fluid is placed, but also one can resect bone which overlies the nervous tissue or push away fascia or muscle etc. The number codes in this figure mean 43=colliculus; 44=cerebro-spinal fluid; 45=example of a collicular device and 46=example of a tiny cerebellar cortical device.

Figure 8:
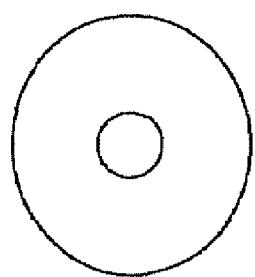
Figure 8:
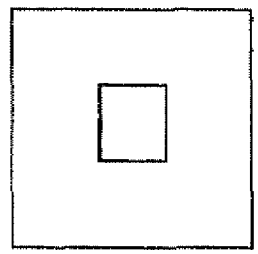
Figure 8:
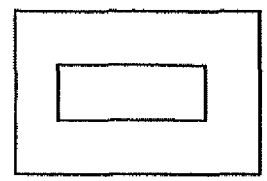
Figure 8:
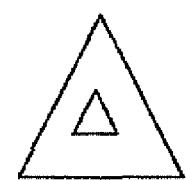
Figure 8:
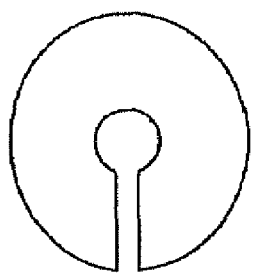
Figure 8:
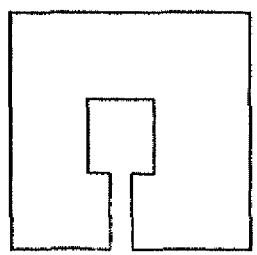
Figure 8:
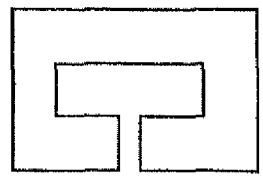
Figure 8:
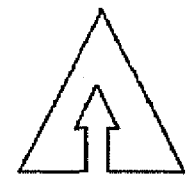

FIG. 8. Is a drawing of the electrical contacts, which can be combined with the thousands or millions of other stimulation and recording contacts in all devices with electrodes described in this invention. The area between the outer circle and inner circle can be the same metal as used in electrodes for nervous system stimulation which are nowadays on the market. The material can for instance be platinum, gold, tungsten, Pt/Ir, stainless steel, Pt/IrN Sfine, with or without metallic, ceramics, diamond like coatings or polymer coatings. Within this area (i.e. within the smallest circle) and outside the outer circle between 1 and several thousands of microelectrodes for recording and stimulation can be placed. The contact can be any form (circle, oval, quadrangle, triangle etc. and some of those forms are depicted in the upper panel) and it has a flat structure. The wires for the microelectrodes can either run behind the contact, or at a pathway which runs through the large contact as depicted in the lower figures.

Figure 9:
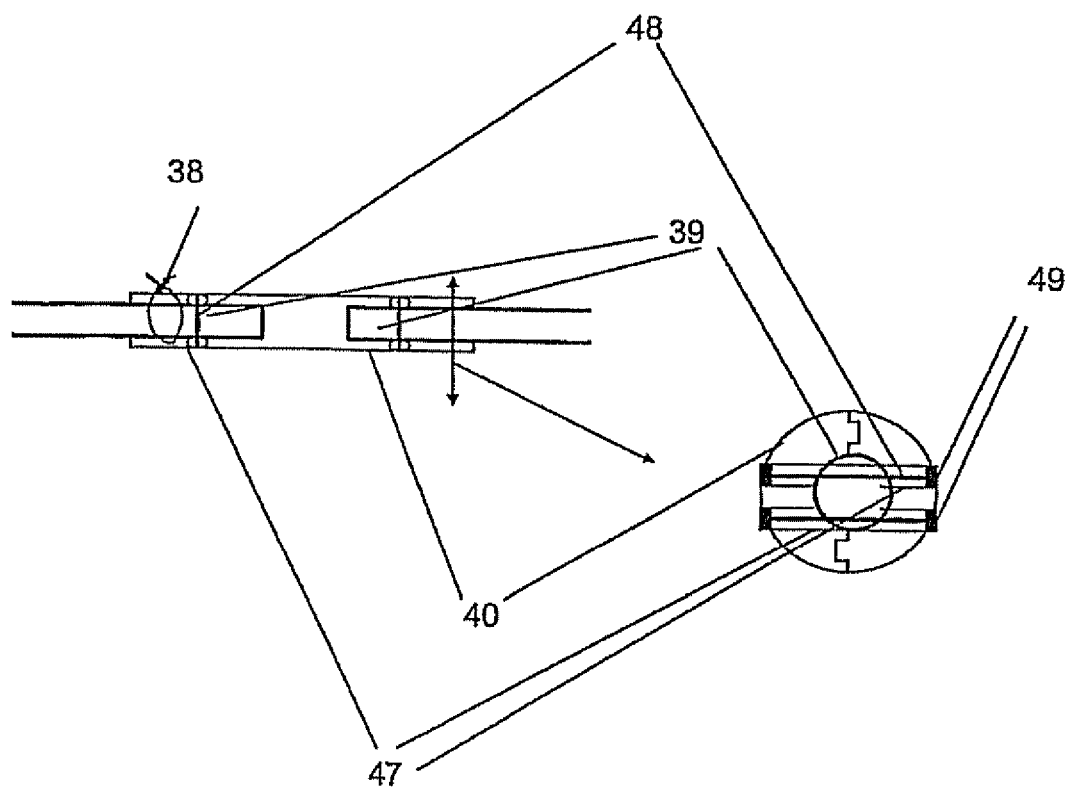

FIG. 9. Is a drawing of a device for reconstruction of an injured tube-like structure of the nervous system, as there are: injured spinal cord, injured nerve root or injured peripheral nerve. The device is the same as the device depicted in FIG. 7.*c*. However, through one or more holes, one or more tiny needles can be inserted. Those needles are fully covered with many (hundreds or thousands) of recording and stimulating micro-electrodes at those sites where the needles make contact with the nervous tissue. The idea in e.g. spinal cord injury is to stimulate and record from the grey matter (e.g. anterior and posterior horn) and white matter. The same strategy can be used as for all devices described in this invention. This strategy can be found under the heading "Practical functioning of the different devices, described in this invention in order to restore function". The needles can be inserted based on the anatomy of the spinal cord as can be visualized on e.g. MRI, where the grey matter and white matter can nicely be seen and based on the knowledge of the position of certain pathways (motor, sensory, autonomic fibres) in space.

The number codes in this figure mean 47=hole in the electrode to insert the needle covered with micro-electrodes for stimulation and recording; 48=the needle covered with micro-electrodes for stimulation and recording; 49=a fixation tool to fix the needle in relationship to the device, e.g. a cap or a screw o any fixation tool so that the needle stays in place; 38=suture; 39=nerve and 40=device.

Figure 10:
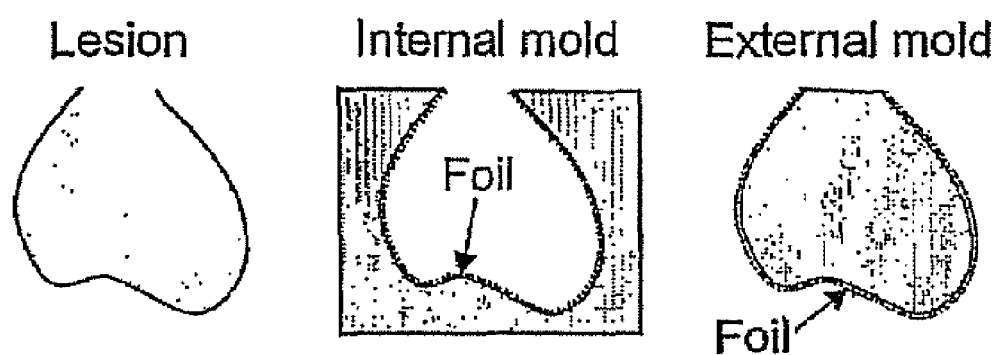

FIG. 10. Shows alternative molding strategy to produce the customized three dimensional electrode: an external mold which can be made for producing the three dimensional foil by casting or spraying or an internal mold that can be made for producing the three dimensional foil by blowing.

Figure 11:
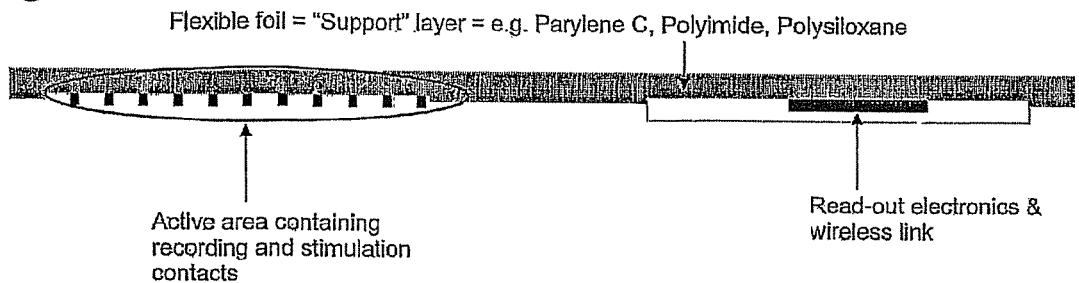
Figure 11:
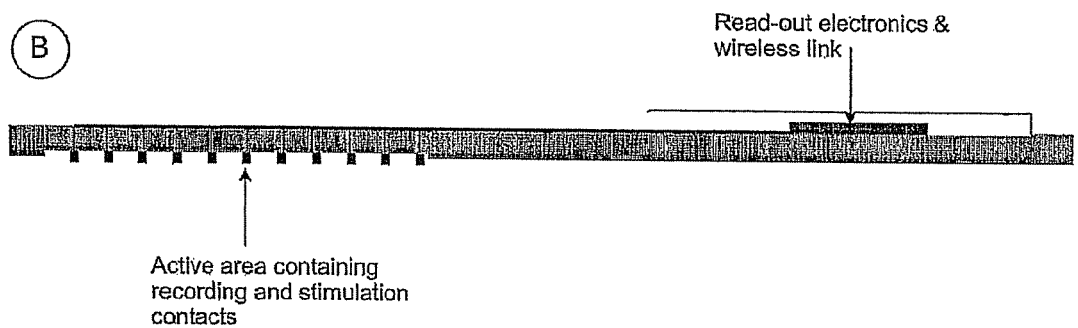

FIG. 11. Demonstrates the localization of the electronic components on the flexible foil: Active area is defined as area of the foil comprising the stimulation and/or recording contacts in direct contact with the lesion healthy border; The contacts on the active area are connected with the read out electronics containing or not a wireless link either on the same side of the foil (A) or through the foil on the opposite side (B)

Figure 1:
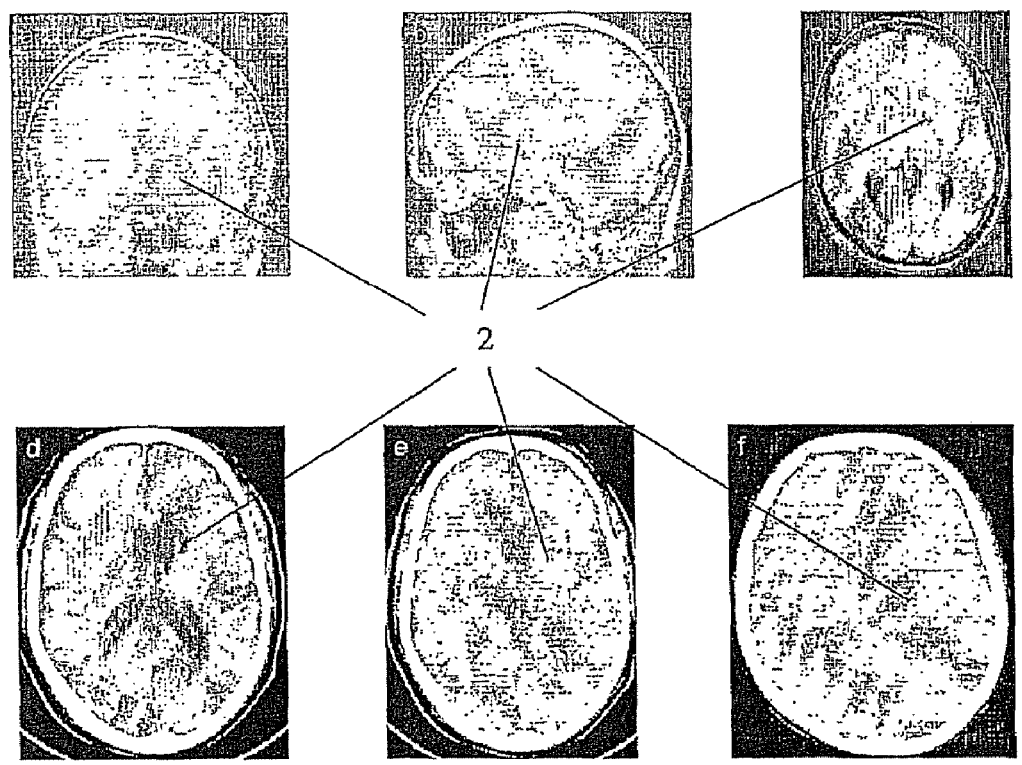
FIG. 1. provides coronal, sagittal and transverse (axial) example brain images of brain lesions (2): a., b. and c. show a stable intracerebral lesion due to a brake of a bicycle which entered the brain after a fall several years before this scan (T1-weighted magnetic resonance imaging) was taken. The patient has dyskinesia (abnormal movements) after this kind of injury. d This computerized tomography scan shows a lesion in the caudate nucleus, e a lesion in the globus pallidus, f in the thalamus.
Figure 2:
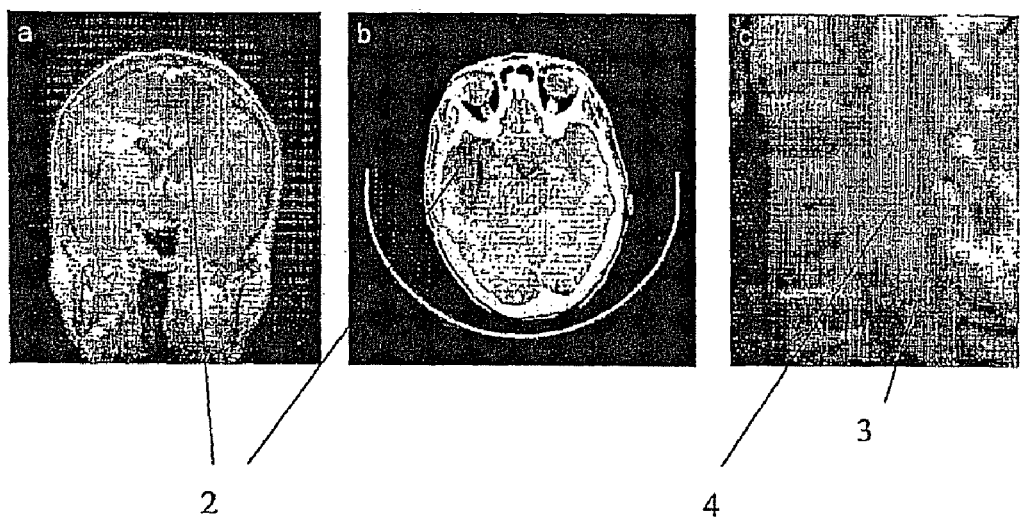
FIG. 2. provides a. a coronal transverse image of a large brain lesion in both hemispheres, and the cavity, which is filled with fluid, is easily accessible from the outside by a trepanation (operation with opening of a reasonable part of the skull). b. a transverse section image of the large brain lesion (2) in one hemisphere, and the cavity, which is filled with fluid is easily accessible from the outside by a trepanation and C. Large lesion hypo-intense on T1-weighted magnetic resonance imaging or dark) in the spinal cord (grey), which causes both sensory and motor loss below the lesion, and both urinary and faecal incontinence. The spinal cord has been marked by the number code 3 and the spinal cord lesion has been marked by the number code 4.
Figure 12:
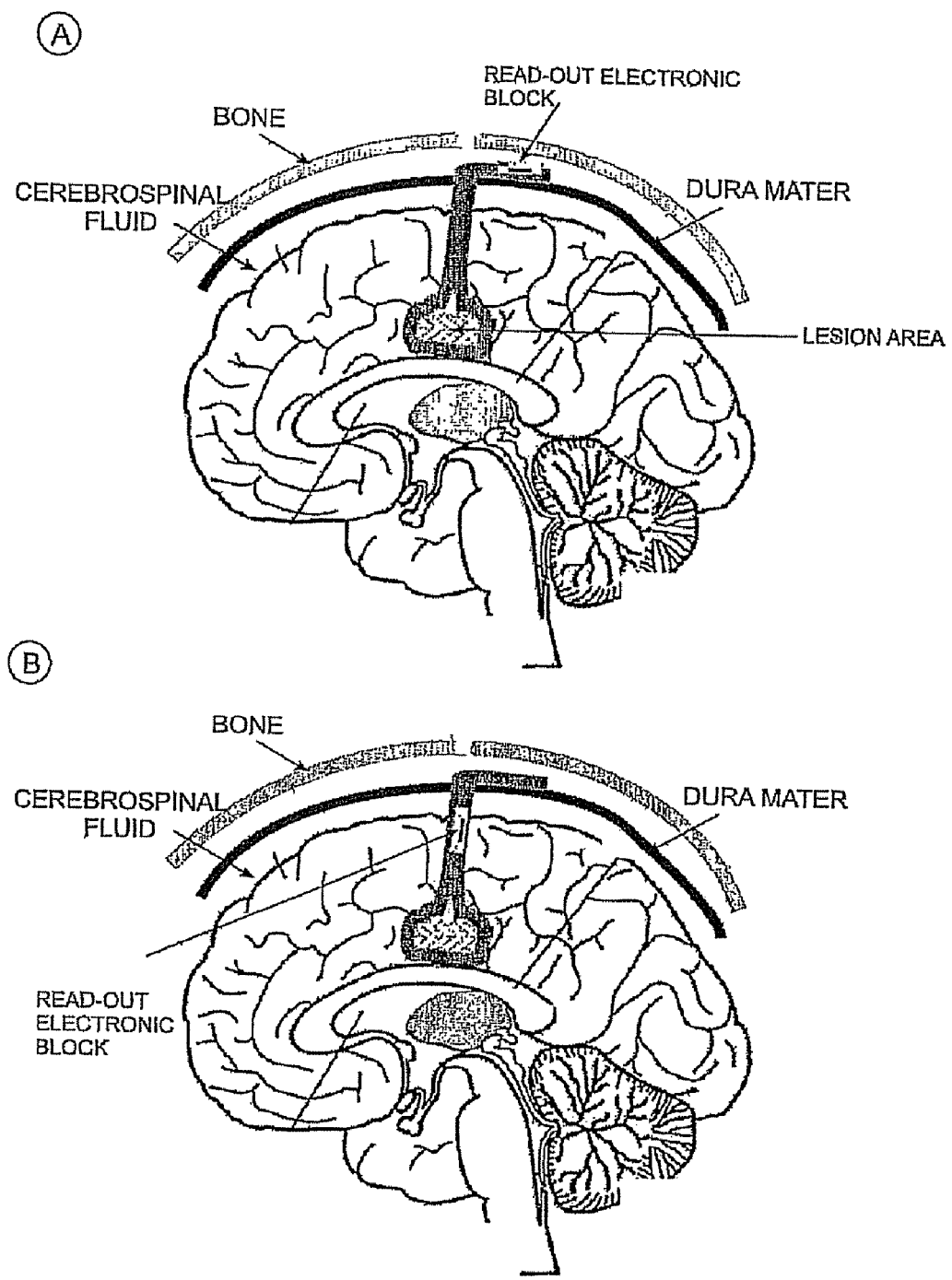

FIG. 12. Is a schematic representation of the implant in the brain—illustrates the potential positions of the readout electronics block (A) above the dura matter (in this case the electronic block is positioned on the same side of the foil as the stimulation and recording contacts—as shown in FIG. 1A; (B) Below the dura (in this case the electronic could be contained inside the active region of the implant or external, with appropriate packaging—not shown).) The preferred position of the readout electronics block will be in the burr hole or outside the skull bone, either subcutaneously or elsewhere in the body FIG. 11. Shows schematic representation of the molding process—in the case of the Method 2 a "glue" layer is covering either the mold covered with the release layer and a biocompatible polymer or the back side of the flexible implant foil.

Figure 14:
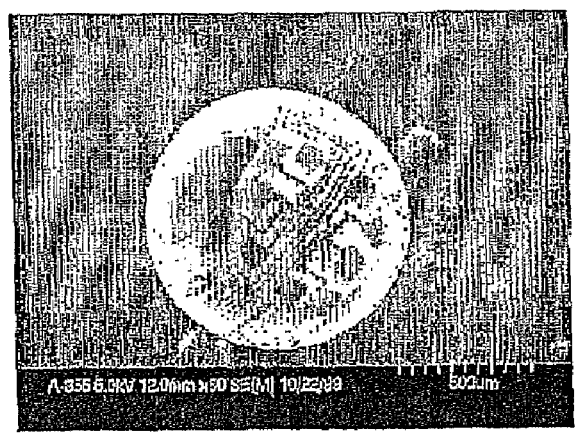

FIG. 14 Metallization patterns on silicon spheres—Ball Semiconductor Inc.

Figure 15:
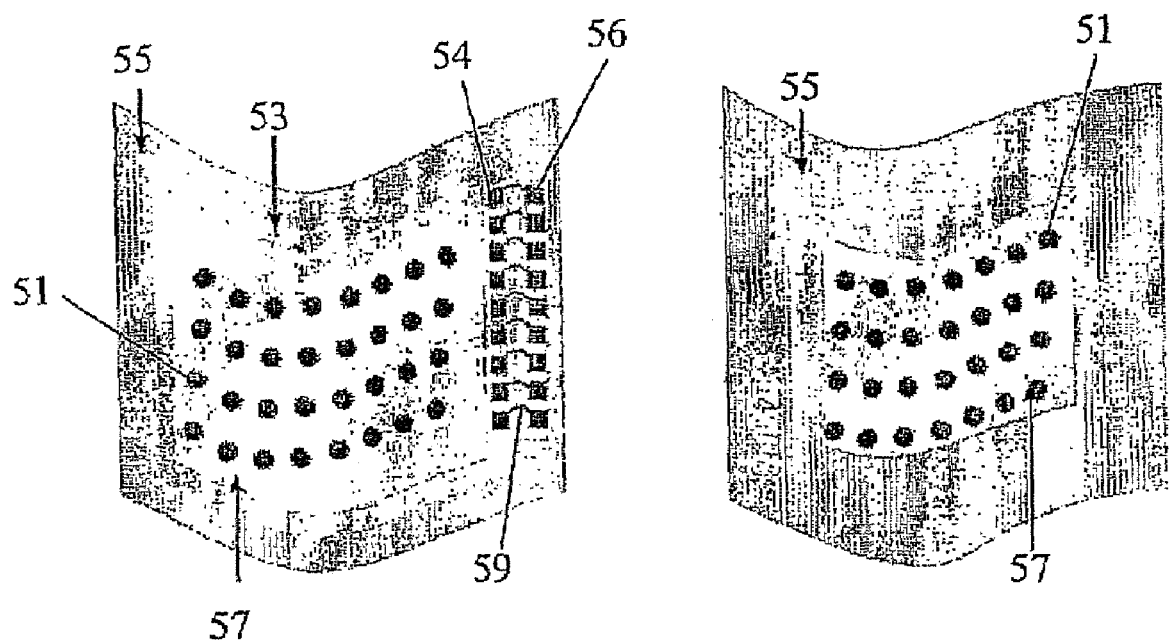

FIG. 15 illustrates two possible packaging methods, i.e. wire bonding approach (left) and flip chip approach (right), for use with a probe according to the present invention. These methods can be used for producing foils that can be shaped into a bridging device to fit in the target cavity of excitable cell tissue by the 3D imaging and rapid prototyping technology described in this application.

Other embodiments of the invention will be apparent to those skilled in the art from consideration of the specification and practice of the invention disclosed herein. It is intended that the specification and examples be considered as exemplary only.

ILLUSTRATIVE EMBODIMENTS OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

The present invention provides a bridging device for inserting in cavities in tissues or organs of an organism for instance stable intracerebral lesions and for restoring interconnectivity or transfer of electrical signals between excitable cell, which bridging device can perform measurements in three dimensions and which has a low electrode impedance and thus a low power consumption. The present invention also provides a method for the manufacturing of such a bridging device. The bridging device will mainly be described by means of a neuro-bridging device suitable for use in brain lesion bridging (BLB). It has, however, to be understood that this is not limiting the invention and that the bridging device according to the invention may also be used for other applications, such as e.g. stimulation of muscles.

The bridging device for stimulation and recording of electrical cell activity according to the invention may be used for repairing the nerve signal transduction or for the treatment of restoration of lost functions of the nervous system causing disorders such as dyskenia, sensory and motor loss, urinary and faecal incontinence. The bridging device for stimulation and recording of electrical cell activity according to the invention may also be used for reconstruction or functional bridging of the injured tube-like structures of the nervous system such as the injured spinal cord, injured nerve root or injured peripheral nerve.

When, in the description and in the claims, the term "recording means" is used, a means is meant which can be used for measuring, indicating, reading, . . . cell activity of excitable cells present in the tissue to be examined or treated, e.g. brain tissue in case of brain lesion bridging (BLB).

Furthermore, the terms "column" and "row" are used to describe sets of array elements which are linked together. The linking can be in the form of a Cartesian array of rows and columns, however the present invention is not limited thereto. As will be understood by those skilled in the art, columns and rows can be easily interchanged and it is intended in this disclosure that these terms be interchangeable. Also, non-Cartesian arrays may be constructed and are included within the scope of the invention. Accordingly the terms "row" and "column" should be interpreted widely. To facilitate in this wide interpretation, there may be referred to "logically organised rows and columns". By this is meant that sets of memory elements are linked together in a topologically linear intersecting manner; however, that the physical or topographical arrangement need not be so.

The surfaces of the bridging device, e.g. neuro-bridging device, that are in contact with the tissues at the edge of cavities, e.g. brain in case of a neuro-bridging device e.g. for brain lesion bridging, are fabricated from or coated with biocompatible materials. The surfaces which are in contact with the brain are the stimulation/recording sites and/or sites of recording and/or sites of stimulation which may be fabricated from noble metals such as e.g. Au, Pt or Ir and the insulating coating (see further) which may be formed of oxides (e.g. IrOx, $Ta_2O_5$, $SiO_2$, $ZrO_2$), $Si_3N_4$, polymers (e.g. parylene C, parylene N, silicone rubbers, polyimides) or biocompatible epoxies.

Each pixel comprises at least one stimulation transducer or micro-electrode for stimulating a part of the tissue, e.g. brain e.g. in case of brain lesion bridging, and at least one recording transducer or micro-electrode for measuring activity of a part of the tissue, e.g. brain for example in case of brain lesion bridging. Each pixel thus comprises at least two micro-electrodes. In the further description, the pixel will be referred to as stimulation/recording sites or sites of recording or sites of stimulation. The at least one stimulation transducer present in each stimulation/recording site or the sites of stimulation is formed by a microelectrode which may comprise a noble metal (e.g. Au, Pt, Ir). Preferably, Pt and/or Ir may be used for the delivery of the stimulation pulses when in contact with excitable cells, e.g. neurons in case of brain lesion bridging. The microelectrodes should be able to deliver monophasic cathodic or biphasic pulses generated by a voltage controlled pulse generator (0 to 20 V stimulus amplitude, 20 to 1000 µsec, for example between 60 and 200 µsec pulse duration and 2 to 1000 Hz, for example between 60 and 200 Hz frequency). In embodiments according to the invention, also a constant current pulse generator may be used for generating pulses.

Field-effect transistors (FETs) may, for example, be used as recording transducers or micro-electrodes for recording of the cell activity. The signal provided by the recording transducers will be further processed by a controller, e.g. a microprocessor unit, which may e.g. be placed somewhere on the dura mater in a burr hole or below the skin. This unit will also provide a required pulse pattern to be applied to the stimulation electrodes. The steering electronics can be completely external to the tissue, e.g. brain in case of brain lesion bridging, or may be distributed between the bridging device, e.g. neuro-bridging device e.g. in case of brain lesion bridging, and an external part thereof. Although the term 'external' is used, this does not mean that the steering electronics are necessarily outside the body of the patient. In case of brain lesion bridging, this also includes that the steering electronics may be implanted not in the brain itself, but e.g. between the skull and the dura mater in a burr hole or below the skin (see further).

Each stimulation/recording site may have a width and length between 5 and 100 µm. Preferably, each pixel or stimulation/recording site may have a size of between 5 and 50 µm, more preferably between 5 and 30 µm and most preferably between 5 and 10 µm. The size of the stimulation/recording sites or sites of recording or sites of stimulation determines the resolution of the bridging device, e.g. neuro-bridging device. Therefore, in order to obtain a good resolution, each stimulation/recording site may preferably be as small as possible because the better the resolution is, the more precise the controllability of the bridging device becomes. However, the smaller the surface area of the stimulation electrode, the higher the charge density will become ($\mu Coul/cm^2$). The charge density determines the amount of current that can be delivered, and this must happen without damaging the tissue where the bridging device is positioned, e.g. the brain in case of brain lesion bridging.

The array comprising the stimulation/recording sites and/or sites of recording and/or sites of stimulation may be a CMOS array, and is bonded to a biocompatible substrate, also called packaging substrate, with a given geometry suitable for implantation in the relevant anatomic target (e.g. STN). According to the invention, 3D field distribution is important and the geometry of the bridging device should enable this. Therefore, ideally, the bridging device, and therefore the substrate thereof, may have the shape of the edge of a target cavity with the active pixels or stimulation/recording sites and/or sites of recording and/or sites of stimulation 51 distributed on the external site (the outer site when placed in the cavity) and thus in contact with the tissue, e.g. the brain tissue. Due to the stimulation transducers and recording transducers of the pixel being located in an array, this array being bonded onto a substrate, the electrical field distribution can be controlled. Furthermore, recordings of electrical activity of excitable cells, e.g. neuronal electrical activity in case the bridging device is a neuro-bridging device e.g. for performing BLB, can be performed in three dimensions. Furthermore, the bridging device has a sufficient flexibility for optimal conformity to the tissue target, e.g. brain target. This may be achieved by folding or bending the flexible packaging substrate. Once the stimulation/recording sites and/or sites of recording and/or sites of stimulation are bonded to the substrate, the flexible substrate comprising the attached array of stimulation/recording sites and/or sites of recording and/or sites of stimulation, e.g. brain lesion bridging and recording or stimulation array, can be introduced as bridging device into the tissue cavity, e.g. brain lesion.

Because the bridging device according to the invention, due to the customised shapes it can take and the distribution of a large number of stimulation/recording sites and/or sites of recording and/or sites of stimulation thereon, has the possibility to perform measurements in three dimensions, the bridging device can work with high spatial resolution and high signal-to-noise ratio. Furthermore, with the bridging device according to the present invention, recordings of the activity of excitable cells, for example, cellular activity in the STN, could be used for providing feedback, allowing the stimulation only while necessary, leading thus to a substantial power consumption saving. Moreover, the bridging device according to the first aspect of the invention is able to perform electrical stimulation and recording of the activity of excitable cells, for example brain lesion bridging and recording, at single cell level which makes it possible to understand the mechanisms responsible for the therapeutic effect of the technique.

It has to be remarked that the bridging device according to the invention is compatible with existing signal processing and control circuitry and implant positioning procedures.

In a second aspect of the invention, a method for the manufacturing of a bridging device according to the first aspect of the invention will be discussed and illustrated in FIG. 15. The method will merely be described for a neuron-bridging device, e.g. for brain lesion bridging. However, it is to be u 20, such as bridging devices to be implanted in lesion of muscular tissue or in cardiac tissue for stimulating excitable cells within these tissues may also be manufactured using the method according to the invention.

In a first step, an array of stimulation/recording sites and/or sites of recording and/or sites of stimulation 51 is formed on a die 53, which may, for example, be a silicon die. Hereinafter, the method for the manufacturing of a bridging device according to the first aspect of the invention will be described for a silicon die 53. It has to be understood that this is not limiting to the invention and that other semiconductor materials, such as e.g. GaAs, SOI (silicon on insulator), can also be used. However, in the case of SOI the method may be adapted in the sense that no thinning step may be needed as SOI can be made thin enough before the start of the manufacturing of the bridging device.

Formation of the stimulation/recording sites and/or sites of recording and/or sites of stimulation 51 onto the die 53 may be performed by means of micro-fabrication techniques known by persons skilled in the art, such as, for example, IC or CMOS standard and non standard processes. The die 53 may have a thickness of between 300 µm and 1 mm, for example 850 µm.

It is an advantage of the present invention that the array of stimulation/recording sites and/or sites of recording and/or sites of stimulation 51 may be applied by a standard process on a standard substrate, as this makes the fabrication process far more easy than making the array of stimulating/recording sites directly on a substantially cylindrical or conical substrate. Contacts 24 are provided using, for example, standard CMOS metallisation processes. Suitable materials for forming the contacts 55 may, for example, be Al or Au or any other suitable noble metal.

In a next step, the die 53 on which the array of stimulation/recording sites and/or sites of recording and/or sites of stimulation 51 is formed may first be thinned down to e.g. 50 µm, preferably down to 25 µm, more preferably down to 10 µm and most preferably down to 5 µm. As already discussed, in case the die is formed of SOI, this thinning step may not be necessary because the SOI die may already be thin enough. In the case that the bridging device would only comprise passive electrodes, e.g. metal lines, it could be processed on all kind of substrates including plastic. However, the signal to noise ration and thus the chronic recording will be poor with such electrodes. Also thin-film transistors have poorer properties compared to silicon transistors. Therefore, preferably standard CMOS processing performed on semiconductor substrates such as e.g. Si, GaAs or SOI substrates may be used according to embodiments of the present invention. Thinning down is performed down to a thickness of the die low enough to make the die flexible. Thinning down may be performed by any suitable method, such as e.g. mechanical or chemical polishing or by a combination of both.

In a next step, the thinned die 53 comprising the stimulation/recording sites and/or sites of recording and/or sites of stimulation 51 is bonded to a substrate 55. The substrate 55 may, for example, comprise biocompatible material such as any of parylene C, parylene N, polyimide, polysiloxane rubber or teflon, but may also comprise a noble metal (e.g. Au, Pt, Ir), titanium, oxides (e.g. IrOx, $Ta_2O_5$, $SiO_2$, $ZrO_2$), $Si_3N_4$ or biocompatible epoxies. The material the substrate 55 is formed of should be such that cytotoxicity and material degradation is prevented when the bridging device is implanted in the tissue, for example the brain in case of a neuro-bridging device e.g. for brain lesion bridging.

The substrate 55 has an area and lies in a plane, the area extending in the direction of its plane. The die 53 comprising the stimulation/recording sites and/or sites of recording and/or sites of stimulation 51 also has an area, the area of the die 53 extending in a direction substantially parallel to the plane of the substrate 55. The area of the substrate 55 may preferably be larger than the area of the die 53 comprising the stimulation/recording sites and/or sites of recording and/or sites of stimulation 51. The die 53 comprising the stimulation/recording sites and/or sites of recording and/or sites of stimulation 51 forms the active part of the bridging device 50.

The packaging or bonding method may be based on either wire bonding or flip chip assembly of the die 53 comprising the array of stimulation/recording sites and/or sites of recording and/or sites of stimulation 51 onto the substrate 55, which is a biocompatible flexible substrate that can be formed in a customised manner to take the shape and dimensions of the edges of a target cavity in a tissue or organ.

The process flows for the wire bonding approach (left hand side) and for the flip chip approach (right hand side) are both schematically illustrated in FIG. 15.

In the wire bonding approach, the die 53 comprising the array of stimulation/recording sites and/or sites of recording and/or sites of stimulation 21 is positioned with its bottom surface 53a to the top surface 55a of the substrate 55, and its contacts 54 are wire bonded, i.e. connected with fine metal wires, e.g. gold wires, to contacts 56 present at the substrate 55, as known by persons skilled in the art. The contacts 54 on the die 53 and the contacts 56 on the substrate 55 are then covered by a biocompatible insulating coating 57. The biocompatible insulating coating 57 may for example be oxides (e.g. IrOx, $Ta_2O_5$, $SiO_2$, $ZrO_2$), $Si_3N_4$, polymers (e.g. parylene C, parylene N, silicone rubbers, polyimide) or biocompatible epoxies. This biocompatible insulating coating 57 is required for passivation reasons. Only the 'active area' of the stimulation/recording sites and/or sites of recording and/or sites of stimulation 51 should be allowed to be in contact with the brain. The rest of the bridging device 50, mainly the electrical connections, are in that way protected to avoid corrosion or other undesirable reactions between the material they are made of and the brain.

In the flip chip approach (right hand side of FIG. 15), a patterned flexible substrate 55 is provided onto a sacrificial substrate 58. The sacrificial substrate 58 may comprise any suitable material such as e.g. silicon, plastics (e.g. polycarbonates, polyethersulphone, polyimides) or glass. Suitable materials should be sufficiently strong and be able to form planar surfaces. Contacts 56 are provided on the top surface of the substrate 55. The die 53 comprising the stimulation/recording sites and/or sites of recording and/or sites of stimulation 51 is then bonded to the top surface of the substrate 55 such that the contacts 54 on the die 53 match the contacts 56 on the top surface of the substrate 55. Optionally, a sacrificial layer (not shown) may be present between the sacrificial substrate 58 and the flexible substrate 55. The sacrificial layer may be, for example, a thin metal layer (e.g. Al, Au), a polymer, an acetone soluble wax or a self-assembled monolayer of molecules that prevent strong adhesion (e.g. silanes, thiols, fluoropolymers). A biocompatible insulating coating 57 is then provided over the die 53 and over the flexible substrate 55. The biocompatible insulating coating 57 may for example be oxides (e.g. IrOx, $Ta_2O_5$, $SiO_2$, $ZtO_2$), $Si_3N_4$, polymers (e.g. parylene C, parylene N, silicone rubbers, polyimide) or biocompatible epoxies. After that, the sacrificial substrate 58 is removed. This may be performed by peeling off the flexible substrate 55. In other embodiments, in case a sacrificial layer was present between the sacrificial substrate 58 and the flexible substrate 55, removing the sacrificial substrate 58 may be performed by removing this sacrificial layer by dissolution in its own solvent, for example, if the sacrificial layer is a solvent-soluble polymer it will dissolve in the given solvent, e.g. acetone-soluble wax can be removed by immersing in acetone.

The die 53 is bonded onto the flexible substrate 55 (wire bonding approach is shown). Fine wires can be between the contacts 54 on the die 53 and the contacts 56 on the flexible substrate 55.

The present invention furthermore includes a computer program product which provides, when executed on a computing device, the functionality of the method for determining a stimulation pattern for application to excitable cells in a tissue, using a bridging device-device according to embodiments of the present invention. Further, the present invention includes a data carrier such as a CD-ROM or a diskette which stores the computer program product of the present invention in a machine readable form and which executes the method for determining a stimulation pattern for application to excitable cells in a tissue using a bridging device-device according to embodiments of the present invention when executed on a computing device. Nowadays, such software is often offered on the Internet or a company Intranet, e.g. a hospital internet, for download, hence the present invention includes transmitting the stimulation pattern determining computer product according to the present invention over a local or wide area network. The computing device may include one of a microprocessor and an FPGA.

The present invention furthermore provides a device for determining a stimulation pattern for application to excitable cells in a tissue by means of a bridging device according to the first embodiment of the present invention. The device comprises:

a bridging device according to the first embodiment of the present invention for recording electrical activity of excited cells and generating corresponding activity signals, processing means for comparing the generated activity signals with pre-determined activity signals for the excited cells, and stimulation pattern determining means for generating, from said comparison, stimulation pattern parameters of the stimulation pattern. The stimulation pattern parameters may comprise frequency and/or amplitude and/or pulse duration.

It is to be understood that although preferred embodiments, specific constructions and configurations, as well as materials, have been discussed herein for devices according to the present invention, various changes or modifications in form and detail may be made without departing from the scope and spirit of this invention.

EXAMPLES

The device of present invention to exactly fit the lesion cavity or at least to have its electronic stimulating or recording sites contacting the excitable cells (either magnetic resonance imaging—(MRI)—compatible or not) is designed such that it just fits the wall of a nervous system cavity, which can be regular or irregular in structure.

The minimum volume of the lesion and the 3D shape of the region can be critical factors for the electronics. For instance the lesion has have the physical dimension allowing to accommodate the required electronics. The current minimum electrode size is 1-5 um if simple metal electrodes are used and if active electronics is placed on each contact point, the current minimum pixel size is increased to 5-10 um. It is difficult to have electrodes in regions of the implant surface with very high aspect ration (i.e. mountains and valleys close to each other). Nevertheless, an equal distribution of the electrodes is not always not required.

A suitable means is a balloon-like device (in the meaning of a sac or a foil forming a hollow body covered with stimulating and/or recording microelectronic elements that is inserted into a cavity), produced to fit exactly the cavity, e.g. lesion cavity. The cavity can be a cavity which already exists for a long time, or a cavity created during surgery, e.g. at the moment of resection of a benign tumour. This design is possible by performing medical imaging with computerized tomography (CT scan), magnetic resonance imaging (MRI) or an other imaging modality visualising the nervous system of the patient (positron emission tomography (PET), single photon emission tomography (SPECT), magneto-encephalography (MEG) etc.). The three-dimensional structure of the cavity will thus be visualized and based on this 3-D-dataset, a hard 3D structure or mold of Resin or other material can be created using already existing techniques (e.g. Rapid prototyping & manufacturing technology and medical imaging technology of companies such as Materialise and Medicim NV ((Oralim®), 3D Systems soft, VIDX Scan Imaging Software (Evex Analytical Instruments), Zmode, Vis5D, VIDA). Using such software, very fine details can be integrated in the digital design of the mold. Once the computer model of the mold is ready, the mold can be produced directly by layer manufacturing techniques, such as Selective Laser Sintering (SLS), Selective Laser Melting (SLM), Stereolithography (SLA), Fused Deposition Modeling (FDM), Inkjet based systems, Three Dimensional Printing (3DP), Laminated Object Manufacturing (LOM); Laser Engineered Net Shaping (TM) (LENS®) etc. These Rapid Manufacturing processes have the advantage of geometrical freedom and very small features can easily be made. The molds are preferably composed of a metal, the metal mold being produced by SLS or a polymer, preferably PC-ISO Polycarbonate, mold that can be produced by SLA. When using the molding strategy to produce the customized three dimensional electrode, two methods are possible.

On top of this hard material or mold, which perfectly resembles the 3D structure of the cavity in the central nervous system, a balloon-like or cloth-like structure can be created which perfectly fits, just like one makes a shoe on top of a wooden base structure. In an external mold (FIG. 10) the three dimensional foil (balloon or balloon-like structure) is obtainable by casting or spraying and on an internal mold (FIG. 10) the three dimensional foil (balloon or balloon-like structure) is obtainable by blowing.

The balloon or balloon-like structure should contain on the outside between 10 and many thousands or even millions of stimulating microelectrodes and recording microelectrodes. Preferably stimulating microelectrodes and recording microelectrodes are placed in an order, so that the relative position of each electrode in space remains known. The order can be Cartesian, but it can have any other order. Either the whole outside or only part of the outside of the balloon or balloon-like structure can be covered. The thickness of the wall of the balloon or balloon-like structure can be subtracted from the volume of the nervous tissue cavity by simply subtracting a distance (e.g. 1 or 2 mm) of the whole surface with a software technique which is already routinely used in the Brainlab software for radiosurgery planning. The device can be inserted through a trepanation (large opening of the skull) or still easier by means of a simple burr hole in the skull, using a cannula of which the diameter is large enough to pass the balloon or balloon-like structure through. The diameter will depend on the maximal diameter and 3D-complexity of the lesion cavity. In case of a small lesion cavity, a small diameter cannula will suffice. There are at least 3 different sorts of balloons for human use or for use in non human mammalians.

Example 1

First Embodiment of a Microelectronic Carrying Balloon Device

Figure 3:
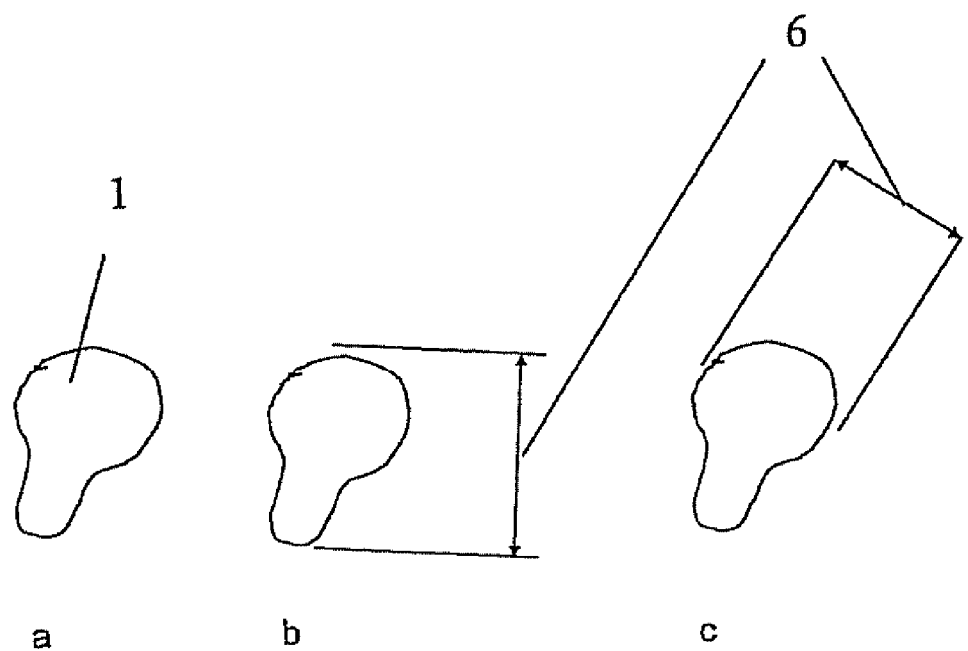
FIG. 3. provides drawings with a schematic view showing a. lesion cavity (1). b. lesion cavity with a cannula coming from lateral. c. lesion cavity with a cannula coming from more above. In this case the diameter (6) of the cannula is smaller than in FIG. 3.b.

The balloon or balloon-like structure can be a composed of liquid tight foil so that when filled with a fluid which it does not leak. This fluid can be a saline, and preferably this fluid can be silicone (e.g. Dow Corning 732 silicone). In yet another embodiment of present invention the balloon or balloon-like structure is filled with a hard material, and in this case the assembly can still hardly be called a balloon or balloon-like structure, but the hard piece, which has the 3D-dimensions of the lesion, is suitable for the purpose of present invention. The device is inserted into the lesion cavity through a cannula with a diameter at least as wide as the diameter of the device, which also depends on the direction of insertion of the device. This is explained in FIG. 3. The direction by which the cannula reaches the lesion is not only determined by the 3D-structure of the lesion, but also by the surrounding brain structures and blood vessels. It is possible to make an approach through certain less important brain areas, and not possible to come through highly functional brain areas. Usually it is not possible to go through regions which contain important blood vessels.

The microelectrodes for recording and stimulation are all on the outside of the balloon or balloon-like structure. The cables and stimulator are inside the balloon or balloon-like structure. Optionally there is a wireless connection between the stimulator and a computer, which is either implanted somewhere else in the body (e.g. subdurally, in the burr hole or subcutaneously) or is external to the body.

Example 2

Second Embodiment of a Microelectronic Carrying Balloon Device

Figure 4:
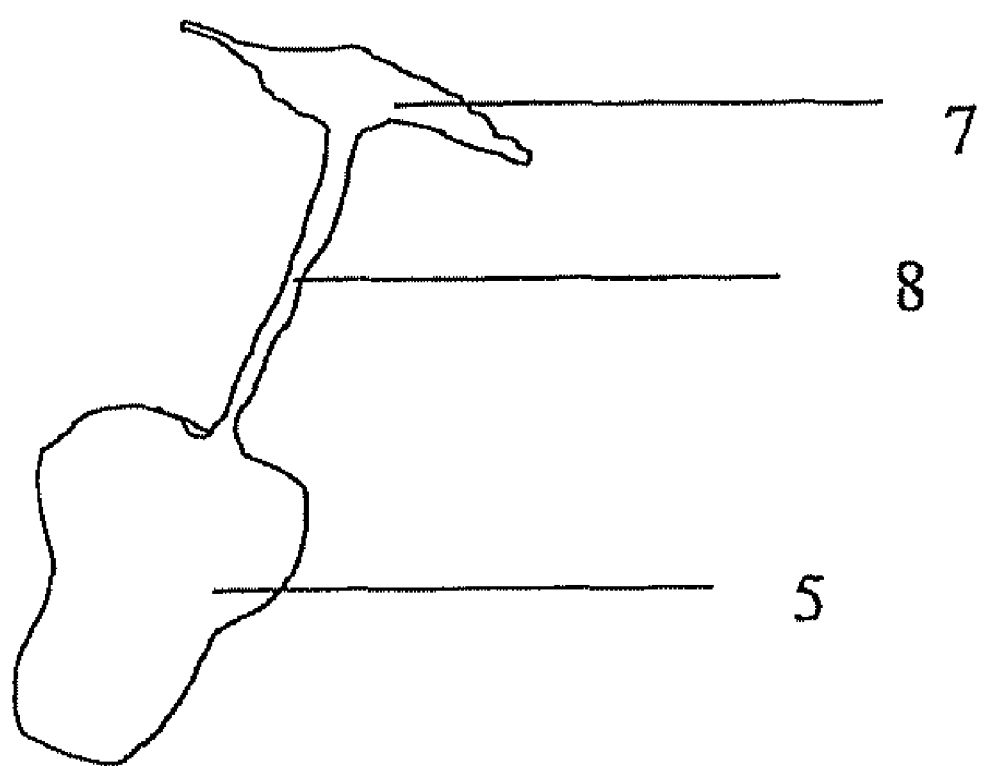
FIG. 4. provides a drawing with a schematic of the balloon or balloon-like structure which resembles the 3D-structure of the lesion cavity is connected with a catheter and a device to fill the balloon or balloon-like structure or to aspirate the balloon or balloon-like structure. Both the catheter and the device to aspirate the balloon or balloon-like structure are already available in the art. It can for instance be a catheter for ventriculo-external shunt (e.g. ventricular catheter 20 cm (which can be trimmed), Integra Neurosciences Implants S.A., 2905 Route des Dolines, 06921 Sophia Antipolis, Cedex. France, or ventricular catheter, Codman, Johnson & Johnson, Raynham, Mass., 02767-0350 USA) and a reservoir (type Omcana reservoir or Accu-Flo® CSF Reservoir 14 mm, ref 82-6100, Codman), connected to the balloon or balloon-like structure by means of a simple metal connection piece and 2 sutures of Mersilene or other non-resorbable biocompatible material. This is known to neurosurgeons, working in the field of ventricular shunts and intrathecal chemotherapy. The catheter can be of any diameter, smaller than the diameter of the cannula which was used for insertion of the balloon or balloon-like structure. The device to puncture can be placed in the burr hole, subcutaneously or anywhere else in the body. If the device to puncture is placed subcutaneously, the ventricular catheter preferably makes a 90° angle. This kind of equipment already exists. The balloon or balloon-like structure can be inserted by a cannula with a smaller diameter than the one shown in FIG. 3, because the balloon or balloon-like structure can be made larger after insertion of the device through the cannula. The device to fill or aspirate from the balloon or balloon-like structure has been marked by the number code 7, the catheter by the number code 8 and the balloon or balloon-like structure, which resembles the 3D-structure of the lesion cavity has been marked by the number code 5.

The balloon (with the same shape and on the outside of which are a similar number of the 2 different electrodes as under example 1) is connected with a catheter which can be laid into the trajectory where the cannula passed during the procedure of insertion of the device. This catheter (e.g. ventricular catheter 20 cm (which can be trimmed), Integra Neurosciences Implants S.A., 2905 Route des Dolines, 06921 Sophia Antipolis, Cedex. France, or ventricular catheter, Codman, Johnson & Johnson, Raynham, Mass., 02767-0350 USA) can be connected with a device which can be filled by simple percutaneous puncture (type Omcana reservoir or Accu-Flo® CSF Reservoir 14 mm, ref 82-6100, Codman). In case the volume of the implanted device decreases due to leakage of the device, or if there will be an insufficient contact between electrodes and brain tissue, one can puncture the device and add liquid into the balloon or balloon-like structure. In case the device will compress the brain too much, some fluid can be aspirated just by subcutaneous puncture. This is explained in the next FIG. 4. The balloon or balloon-like structure which resembles the 3D-structure of the lesion cavity is connectable with a catheter and a device to fill the balloon or balloon-like structure or to aspirate the balloon or balloon-like structure. Both the catheter and the device to aspirate the balloon are available in the art, as described above in this paragraph, and can be a catheter for ventriculo-external shunt and a reservoir, connected to the balloon or balloon-like structure by means of a simple metal connection piece and 2 sutures of Mersilene or other non-resorbable biocompatible material. This is known to neurosurgeons, working in the field of ventricular shunts and intrathecal chemotherapy. The catheter can be of any diameter, smaller than the diameter of the cannula which was used for insertion of the balloon or balloon-like structure. The device to puncture can be placed in the burr hole or subcutaneously. In the last case the ventricular catheter makes a 90° angle. This kind of equipment already exists. The balloon or balloon-like structure can be inserted by a cannula with a smaller diameter than the one shown in FIG. 3, because the balloon or balloon-like structure can be made larger after insertion of the device through the cannula.

The microelectrodes for recording and stimulation are all on the outside (on the outer surface) of the balloon or balloon-like structure. The cables and stimulator are inside the balloon or balloon-like structure. There is a connection, preferably a wireless connection, between the stimulator and a computer, which is either implanted somewhere else in the body (e.g. subdurally, in the burr hole or subcutaneously) or is external to the body. It is also possible to provide a second catheter coming from the balloon or balloon-like structure into the place where the cannula passed through the brain tissue or to the burr hole or to any other place in the body or even via an external lead to connect to a computer outside the body.

Example 3

Third Embodiment of a Microelectronic Carrying Balloon Device

In the case of large, irregular cavities it can be necessary to push certain parts of the balloon or balloon-like structure (which again resembles the 3D-structure of the lesion cavity) from the inside to the outside, in order to provide a good contact between the outside wall of the balloon or balloon-like structure (i.e. where the electrodes are situated) and the nervous tissue. Therefore it can be of help to push with 1 or more straight or bent stylets (or made of any other stiff or flexible material or plastic) with a defined resilience, which are designed, based on the anatomy of the lesion of the patient now being operated, to fit exactly in the extreme corners in such a way that the balloon or balloon-like structure fits nicely to the wall of the cavity. In the case the stylets are not straight, they can be made out of such material that they can be straight as long as they are in the straight cannula. However, as soon as they are pushed beyond the cannula to bring the balloon or balloon-like structure in place, they are bent in a direction as planned by the computer. The direction of the bent can be indicated by a little mark at the level of the grip of the stylet, e.g. a mark pointing anteriorly.

The insertion of the device is shown in FIG. 5a to 5i.

After having made a burr hole, a cannula with large stylet, which fills the entire volume of the cannula, with a blunt tip, is inserted into the brain, using a classical stereotactic approach. This means that the surgeon knows exactly where in space this cannula is situated. Because the surgeon also knows exactly where the 3D-lesion cavity is situated, the surgeon will also know the position of the cannula relative to the lesion cavity (FIG. 5.a.).

Consequently the large stylet with a blunt tip is withdrawn from the cannula (FIG. 5.b.).

Then the folded balloon or balloon-like structure (which is constructed as explained in illustrative embodiments of the invention and Examples) is inserted into the cannula. Different stylets have been fixed to the inside of the balloon or balloon-like structure, just at extremities of the balloon or balloon-like structure. This can be produced based on the 3D-structure and dimension of the lesion cavity as visualized by imaging techniques. The balloon or balloon-like structure and stylets are surrounded by a hard, biocompatible tube (e.g. a polyamide tube), which fits just the inside of the cannula. The base of this tube is fixed to the balloon or balloon-like structure. The top of this tube has screw thread, directed to the inner lumen, in order to be able to close the balloon or balloon-like structure later-on. On the outside of the top of the tube are some irregular structures (e.g. 3 pins) which can immobilize the tube into bone cement which will be applied later-on in the burr hole. The stylets have a desired resilience but are about straight as long as they remain in the stiff tube. The preconditioned resilient nature helps to exactly position the outer end of the stylets at the extreme corner of the balloon or balloon-like structure when positioning the balloon or balloon-like structure in a target cavity. However, once they will be pushed down, they will take on a posture as planned after having analyzed the data of the 3D imaging of the lesion cavity. The correct position of each balloon or balloon-like structure extremity is important. Therefore it will be necessary to mark every stylet and also the tube in order to enable the surgeon to orient the device correctly. One of the possible strategies can be to mark the anterior direction on both the grip of the stylet and the top of the screw thread, although it is evident that there are plenty of other possible ways of marking the instruments in order to provide good orientation. The number of the stylets depends upon the number of extremities of the 3D-volume and can vary between 1 and 20 or more, but the less stylets, the easier the concept (FIG. 5.c.).

The length of the hard extension of the balloon or balloon-like structure depends upon the distance between the lesion and the skull, and this length can be obtained from the imaging data, just like planning a stereotactic intervention. This procedure is known to stereotactic neurosurgeons.

Consequently, the stylets have been pushed down (FIG. 5.d.) The cannula has been removed and some biocompatible material (e.g. Oxycell) can be (but does not have to be) placed between the hard extension of the balloon or balloon-like structure and the bone to prevent later-on the bone cement from entering below the dura mater (FIG. 5.e.). Then bone cement is added on top of the biocompatible material (Oxycell), and the surgeon waits until the bone cement is hard, which usually takes 5 to 10 minutes, but can take longer, depending on which bone cement is used. In order to provide a good fixation of the hard tube to the bone, it is advisable to make at least holes in the bone at the base of the burr hole.

Consequently the stylets are fixed to the side preferably by pushing the stylets to the side into fixation points for the stylets, which are located at the inside of the hard tube. During this procedure the surgeon watches that the stylet is only fixed once it is located at the correct depth, which is planned pre-surgically and which can be read from millimetre and centimetre markings onto the stylets. Once the stylets are fixed into the fixation points, the rest of the stylets can be cut, either by breaking them, or by cutting them with a cutting instrument (FIG. 5.g.). An example of a fixation point for a stylet is shown, but many types of fixation points are possible and are available on the market (FIG. 5.h.).

Consequently a screw is tightened onto the screw thread. If wanted (in order to improve the fixation of the device to the bone, and this is surely wanted when the device becomes relatively large), additional self-tapping screws can be drilled through the lateral part of the major screw into the surrounding bone. Thereafter a needle can be inserted to inject fluid. Another needle can evacuate air. The needle can be any needle, but preferably a Hueber needle and the device which enables punctures without leakage of fluid can be made out of the same material as used in a Synchromed pump (Medtronic Inc.) or any similar material. The microelectrodes for recording and stimulation are all on the outside or outer surface axial of the balloon or balloon-like structure. The cables and stimulator are inside the balloon or balloon-like structure and/or in the tube. There is a wireless connection between the stimulator and a computer, which is either implanted somewhere else in the body (e.g. subdurally, in the burr hole or subcutaneously) or is external to the body. There can also be an opening in the screw, connected to the inside of the balloon or balloon-like structure, containing all wires, in order to externalize them, either to the rest of the body, or outside the body (FIG. 5.i.).

During the process of production of the balloon or balloon-like structure, the stylets are fixed to the extreme corners at the inside (but these do not need to be fixed), to ensure that the surgeon nicely pushes the extreme corners into the right place, but then they need to be cut with scissors or any other cutting device which cuts the material it is made of. Those stylets can also be fixed to the inside of the balloon or balloon-like structure into the extreme corners in a way that these can still be unscrewed or detached by means of a screwing device or a small hook or any detachable system. The stylets can also be replaced by a simple stylet-like instrument which the surgeon holds freely in the hand and uses to push the balloon or balloon-like structure until it touches nicely the brain tissue. This procedure can also (but does not have to) be performed in an open MR-machine, to make sure the balloon or balloon-like structure nicely touches the wall of the lesion cavity. On top of the hard extension of the balloon or balloon-like structure which remains in place, a device can be screwed, which perfectly fits the burr hole, and which can be used for puncturing, and if ever necessary, to approach the balloon or balloon-like structure from the inside by means of stylets. In that case the device needs to be unscrewed.

The device for fixing the cannula to the bone can be made in different forms. One possibility is depicted in FIG. 5 i.

The 3D-structure of both balloon or balloon-like structure and cannula can be planned and developed for each patient separately based on the medical imaging in advance of the actual implantation procedure, as discussed earlier, but can also be copied from another patient, if the anatomy of either the balloon or balloon-like structure or the cannula or of both is similar to the one of the patient to be operated.

In examples 1, 2 and 3 the stimulating and recording electrodes are smaller than the size of a neuronal body. All electrodes are connected to a stimulator, which is either situated inside the balloon or balloon-like structure, or in the canal made by the hard extension of the balloon or balloon-like structure, in the burr hole or subcutaneously close to the burr hole or at a distance from it, connected by subcutaneous cables. There are also connecting pathways between the electrodes and the stimulator/recorder. The stimulator/recorder is driven by a battery which is as long-lasting as possible and as small as possible or rechargeable or it is driven by a radiofrequency system.

The wall of the balloon or balloon-like structure has to be flexible, preferably not very stretchable, although it will not be a problem if it were a little stretchable. The 3-D-position of each electrode will be known by adding markers (e.g. stars, points, numbers, letters, arrows etc.) into the wall of the balloon or balloon-like structure which can be detected in MRI. As the relative position of each electrode to each marker is known, and the position of each marker can be visualized on <1 mm thin MRI-slices, the position of each electrode in relation to the surrounding nervous tissue will be known.

Of course the whole system can be sterilized, preferably gas-sterilized for reasons of sterility before implantation of the device. Whenever it will be necessary to remove the balloon or balloon-like structure (for reasons of infection, or for any other reason) the device can easily be removed by opening the skin on top of the device, untightening the screw, loosening the stylet connections or cutting the stylets and withdrawing the device.

Instead of using the complex stylets, one can also use a simple straight or bent small instrument in the form of a stylet to manually push the balloon or balloon-like structure wall in place, either under direct vision, or using exactly the same technique as shown in the figures, but without fixation of the stylets to the balloon or balloon-like structure wall. Therefore the stylets can easily be removed after insertion of the stylets. Another possibility can be to have a second stylet inside each stylet. Once the balloon or balloon-like structure is in place, the second stylet can be pushed 1 or 2 mm further, and this deblocs the fixation of the stylet to the wall of the balloon or balloon-like structure. Therefore the connection between stylet and balloon or balloon-like structure wall needs to be made such that this simple mechanical mechanism is possible (available on the market). With this mechanism it is possible to remove the stylets completely once the balloon or balloon-like structure is in place. The balloon or balloon-like structure will remain close to the nervous tissue by injection of the fluid after locking the screw. The volume which needs to be injected can easily be measured, as the 3D-volume is known by the software. If this turns out to be a difficult measurement, a styrene example of the 3D-volume can be made, and placed in a water bath with known volume. The volume displaced water is the volume of the 3-D volume of the lesion in the brain.

Example 4

Practical Functioning of the Different Devices, Described in this Invention in Order to Restore Function Visualisation of the Anatomy of the Nervous System:

A possible strategy to start the approach will be to use diffusion tensor imaging technique (DTI), which is one of the MRI-techniques. If one shows one or more fibre bundles with DTI at the border of the cavity, one should be able to know approximately which electrodes are very close to that fibre bundle by measuring on the MRI image or in a software program for stereotactic neurosurgery (like the one from Brainlab) the distance between the fibre bundle at the edge of the cavity and 3 neighbouring markers. Using DTI one can detect where those fibres come from and thus get also anatomical information on their origin. But DTI is not a prerequisite for the functioning of the device. Information of the pathways can also be obtained by classical MRI techniques like T1 and T2-weighted images, and even CT scan, simple anatomical atlases and even without all this information the device will still be able to function, but one can more easily achieve the goal (which is "restoring nervous system function") by using some information of the anatomy of cells and fibres (axons and dendrites).

Recording with All Recording Microelectrodes Upon an External Stimulus

It can be that one will not be able to detect any spikes in damages fibres. However, neuronal cell bodies, lying close to those damaged axons and which can make contact with the still intact parts of the damaged neurons, can be influenced by the firing of those cells (cell body, axons or dendrites). Also, one can detect activity from some healthy neurons, which have about the same function as the dead ones. Depending on the pathways under study (motor, sensory, limbic, auditory, visual, gustatory pathways, etc.) one can provoke an external stimulus which will likely produce spikes in those regions. E.g. if the motor pathway is interrupted, but the cell bodies at the level of the motor cortex are still intact, it is likely that the axons which lie in between the cell bodies at the level of the motor cortex and the cavity wall, will remain alive and functional. An axon however which is not connected to a cell body anymore is expected to dye by Wallerian degeneration. Asking the patient to think of a movement, which the patient cannot perform because of the lesion, can still induce spikes which can be detected at the site of the lesion, or in other words, at the cavity wall. All the recording electrodes which can detect signals which are influenced by the process of thinking of performing a certain motor activity can then be mapped by a simple detection computer program. Thinking once and recording once will not be enough. This process needs to be repeated and compared to conditions when the patient is at rest (i.e. not thinking about performing a certain motor activity) until the signals are reliably shown to be in clear relation with the process of thinking about performing a certain motor activity. The computer software can be designed to take the results of several trials (e.g. 10 or 20 or 100 or even more trials) into account and then one can continue with those recording microelectrodes which most frequently record a signal which is in relation with the imposed stimulus.

It can however be that no signals are recorded at the level of the lesion wall. In that case one can add a second electrode somewhere else (in the given example it can be on top of or in the motor cortex itself) for the recording. The same trials (in the given example: thinking about a certain movement versus not thinking about it) can then be performed.

Study of the Effect of Stimulation with One or More Stimulating Electrodes or Several Groups of Stimulating Electrodes In a next step one can stimulate one or more stimulating electrodes or several groups of stimulating electrodes at different amplitudes, pulse widths and frequencies with either block wave pulses similar to those produced in the Medtronic, ANS or Bion neurostimulators and detect eventual clinical results (e.g. a motor contraction). Again the 3-D-coordinates of the stimulating electrodes can be easily located using the same technique as with the recording electrodes. Different stimulation parameters can also be used, like stimulation as described by Prof. Tass (Peter A Tass, Nonlinear phenomena in complex systems, 2002, Vol. 5, No. 4, pp. 470-478), or administration of a signal that uses the same frequency and/or amplitude and/or pulse width as the recorded signal from one microelectrode or of another microelectrode or a mathematical calculation of some or all of the relevant recorded signals. Another possibility is to administer a random signal mimicking a biological signal.

Connecting Recorded Information with the Stimulating Microelectrodes

The next step will consist of activating the relevant stimulating electrodes (e.g. those that produce a motor response) upon reception of spikes in relevant recording electrodes (e.g. those that record spikes upon thinking of a motor contraction). The relevant stimulation electrodes can produce then blocked pulses, similar to those produced in the Medtronic, ANS or Bion neurostimulators, but can also stimulate with the same stimulation parameters (especially frequency) as the incoming signal recorded in the relevant recording electrodes. In this way a signal which mimics the natural signal is given to the stimulated neurons.

Suitable Applications

It is evident that the example of restoring a motor pathway was only given as a simple example, but it holds the possibility to restore any pathway or a combination of different pathways in the nervous system at the same time, or even a complex network. This is achieved by comparing a series of recordings of brain signals or brain functions in an experimental condition (e.g. thinking about a movement, trying to remember something, trying to look, thinking that one feels something, trying to concentrate, trying to laugh, trying to speak, trying to calculate, etc.) with a series of recordings in a control condition (condition at rest). Preferably those conditions are done in a random order or pseudorandom order, but this is not essential. Those recording electrodes which clearly produce different signals between experimental and control condition can provide the stimulus which steers the stimulating electrodes, which provokes then the final act (producing a movement, remembering, seeing something, feeling, concentrating, laughing, speaking, calculating, etc.). The connection between recording and stimulating electrodes is simply made by the stimulator/computer.

Example 5

A Device Consisting of a Plate with Multiple (e.g. Hundreds) of Stimulating and Recording Electrodes on Both Sides of the Plate for Testing Paradigms in Animal Experiments The device is a plate with a multiple (hundreds) of stimulating and recording electrodes on both sides of the plate. It can be inserted in the nervous system (usually brain, but it can be any part of the nervous system) of non human animals (mice, rats, etc. but also large animals until monkeys). By inserting it in the nervous system it damages the nervous structures and interrupts the axons and dendrites and damages the cell bodies of the nervous system. The most evident first approach is inserting such a plate electrode in the grey and white matter of the brain. Then recording and stimulation can be tested as discussed above under the heading "Practical functioning of the different devices, described in this invention in order to restore function". Depending on the place where the device is inserted in the nervous system, different systems or combinations of systems can be tested. For example, if one wants to try to reconnect the motor system, then one inserts the electrode somewhere in the motor system. One detects via all microelectrodes which signal is in relation with the imposed stimulus. Asking the animal to think of performing a movement is not possible. But one can for instance train before insertion of the electrode to take with the right forepaw a certain object upon ringing a bell. When the electrode is inserted into the motor pathway for the right fore paw, thereby destroying this pathway, it can well be that signals will be recorded by the recording microelectrodes when ringing the bell and while the animal is trying to lift the fore paw, but without succeeding. Of course, control conditions can be added to this design.

On the other side of the electrode stimulation can be performed in order to try to evoke a motor response. Once this motor response has been obtained, the relevant recorded signals can serve as trigger for the stimulation as discussed above under the heading "Practical functioning of the different devices, described in this invention in order to restore function".

Example 6

A Device Consisting of a (Puzzle-Like Set of) 3-D-Volume Structure(s), which are Either Hard (Like Methyl Metacrylate) or More Flexible (Like Silicone)

Just like during the construction of the balloon or balloon-like structure the 3D-volume of the lesion cavity is known by imaging and the 3D-structure is reconstructed using available techniques (Materialise, Medicim, and Nobelbiocare). The idea is to replace the lesion volume, which is filled with cerebro-spinal fluid, by a hard structure. It can consist of one piece, but usually it will be necessary to decompose the 3D-volume into 2 or more pieces (in the FIGS. 6*a-g,* 4 pieces are shown, but the puzzle can be composed of up to 20 or more pieces). As the 3D-structure is known before the surgical intervention, it is possible to number the pieces of the puzzle one by one (in the figures pieces 1, 2, 3 and 4) so that it is easy for the surgeon to place them in the lesion cavity in the right order. Again the stylets can have markings in mm or cm and a mark to show e.g. the anterior direction, in order to be able to orient the piece in 3D. The pieces of the 3D-puzzle cannot be larger in transverse diameter (FIG. 6 *g*) than the transverse diameter of the insertion cannula (called tube in the figure). The depth (FIG. 6 *g*) can be larger than the transverse diameter of the tube. The wall of the lesion cavity in the nervous system is shown in FIG. 6 *a*.

Consequently a cannula or tube is inserted through a burr hole just like for the insertion of the balloon or balloon-like structure (FIG. 6 *b*). Then Piece 1 is inserted with the help of an introducer. It is possible to move the introducer up and down and also in medial and lateral direction, as long as the introducer stays inside the tube. Piece 1 is covered with some until many thousands of microelectrodes for stimulation and recording. The side which does not touch the wall of the lesion cavity is not covered with such microelectrodes, but is the side where all wires can leave piece 1.

Inside piece 1 wires can be stored. It is even possible to store a stimulator or many microstimulators in this place (FIG. 6 *c*.). Consequently, Piece 2 is inserted with the help of a second introducer. As is clearly shown in this figure it was only possible to first place piece 1 and then piece 2, and not the other way around (FIG. 6 *d*.). Consequently, Piece 3 is inserted (FIG. 6 *e*.). Then the piece 4 is inserted. This piece does not cover any microelectrodes, but keeps pieces 1, 2 and 3 in place just by its mechanical presence. This piece can have a structure which is a full piece, if micro stimulators can all be placed in pieces 1, 2 and 3. However, it is likely that all stimulators do not fit in there. Then wires and stimulators can be placed in piece 4. It is also possible to bring all wires through the tube (which can either be withdrawn or left in place) and place the stimulators in the tube, in the burr hole, somewhere else in the body or even outside the body. In the last case the best is to connect all wires with extension cables which leave the body at least 10 or 20 cm further away to prevent infection (FIG. 6 *f*.). What is meant by depth and transverse diameter is shown in FIG. 6 *g*. The transverse diameter is measured in a plane perpendicular on the tube, whereas the depth is measured in the plane of the tube.

The introducers can be handled in the same way as with the balloon or balloon-like structure (cut, fixed to the wall of the tube, removed etc.). If the tube is left in place, a similar fixation method can be used as for the balloon or balloon-like structure (FIG. 5.*i*). It is clear that in case of infection or for any other reason, the device can be withdrawn easily piece by piece.

The practical functioning of the device in order to restore function is obtainable in the same way as for obtaining function by use of the balloon or balloon-like structure.

It can happen that one needs to stimulate or record from neurons that are in the healthy tissue not far from the lesion edge. In that case one can have one or more needle-like structures, covered with stimulating and recording microelectrodes, sticking out from the device (e.g. mounted on Piece 1).

Example 7

A Device to Perform Superficial Stimulation which Follows Sulci and Gyri or Other Surfaces of the Central or Peripheral Nervous System Based on Construction with Techniques of 3D Imaging and Rapid Prototyping as Used by for Instance Materialise, Nobelbiocare or Medicim The detailed description of this embodiment of present invention refers to the accompanying figures.

Axial T2-weighted MRI slices through the upper part of the brain, showing cortex with the gyri, sulci, cerebrospinal fluid and blood vessels are shown in FIG. 7 *a*.

The black delineated structure is a manual delineation of the sulcus and the space between the falx (which is made of dura mater), avoiding to enter the cortex and the blood vessels (FIG. 7 *b*). The structure can also be delineated in the adjoining brain slices. When the slices are thin (1 or 2 mm thick slices) a 3D-volume can be created. There exist automatic delineation programs on the market as well. Just like the production of the balloon or balloon-like structure or the production of the electrode made of many pieces, a hard structure with the same 3-D volume can be produced using available techniques of 3D imaging or rapid prototyping Materials, Medcim, Nobel Biocare). On the side of the cortex a number (between 2 and many thousands or millions) of microelectrodes for recording and stimulation are placed. There are no microelectrodes at the side of the falx.

Of course a similar device can also be delineated anywhere on the surface or in superficial or deep sulci (e.g. the lateral sulcus, the Rolandic sulcus, subdurally or subarachnoidally, or even epidurally) and even on and between the folia of the cerebellum or around the brainstem or around the spinal cord or around spinal cord and nerve roots or between the nerve roots of the cauda equina or around an injured nerve. Examples of those last applications are shown in 7 *c*. The differences between these devices and existing devices are the huge number of stimulating and recording micro-electrodes, and the perfect 3D-fit to the anatomical structures, constructed for each separate patient.

A peripheral nerve with an injury (in this case a complete transsection, but it can be a partial transsection as well) is surrounded by the device, which can be made, again based on the 3D-structure as visualized with medical imaging techniques, just as all the devices discussed earlier (FIG. 7 *c*.). The outer part is depicted as a tube, but can be shaped so that it fits the contours of the surrounding muscles, with small holes on the side in order to be able to fix it to the surrounding fascia on top of the surrounding muscles. Between 2 and many thousands or millions of microelectrodes for stimulation and recording, both at the level of the proximal and the distal nerve ending are at the edge between the nerve and the device, both at the level of the transsection and at the cut edge. It is likely that many distal axons are dead due to Wallerian degeneration, but there can be axons which are a life and can still conduct a signal upon electrical stimulation. The difference between this device and existing devices is the multitude of contacts with axons and the availability of recording and stimulating electrodes, which are linked to each other with a computer so that a relevant recording can induce a relevant stimulation. The same strategy as with the balloon or balloon-like structure can be used, and thus, functional bridging of nerves can be achieved. In this way it can be possible to restore motor, sensory and autonomic function.

The device consists of 2 pieces, which can be brought onto each other and kept in place by some non-resorbable sutures like Mersilene or another suture (one of those is depicted in the figure, but one can need several of them). There can be a small canal on the outside of the device to hold the suture. Care should be taken that the nerve is not compressed but nicely fits the cavity inside the device, but as the device construction is based on medical imaging, it should fit perfectly, at least when, as it should be, distortion of MRI-images and partial volume effect of CT-scans are taken into account. T2-weighted images can also over-estimate the dimensions of certain structures and also this should be taken into account.

As depicted in FIG. 9, pins covered with stimulating and recording micro-electrodes can enter the nervous system. In case of spinal cord injury, descending white matter pathways (which lay cranial to the lesion cavity and which still have their neuronal cell body) can be connected to caudally located grey matter. Relying on additional plasticity this strategy can lead to restoration of motor function. In the other direction, ascending white matter pathways (which lay caudal to the lesion cavity and which still have their neuronal cell body) can be connected to cranially located grey matter to restore sensory function. If this would not restore function, white matter tracts can be connected with white matter tracts, or grey matter with grey matter. If recording in white matter at the site of the lesion is not possible, a second electrode can be placed at the level of the still existing cell body or close to a neuron of higher (or lower) order. Also cranially located parts of pathways or grey matter structures can be connected with caudally located parts of pathways or grey matter structures and vice versa.

In peripheral nerves and nerve roots axons can be connected with each other in a similar way. And also here, if recording at the site of the lesion is not possible, a second electrode can be placed at the level of the still existing cell body or close to a neuron of higher (or lower) order. Using this strategy motor, sensory and autonomic functions can become partially or totally restored.

Even more, it can also be possible to have a third device more distally or proximally than the first (and eventual second) device in order to stimulate or record at a more distal or proximal level, with the aim to have the electrode in the neighbourhood of viable relevant neurons to record from and to stimulate. The stimulators can then connect the 2 or 3 recording and stimulating devices. There is even a possibility to have one device at a proximal level of a nerve and 2 distal devices at the level of 2 branches of the nerve, or to provide direct muscle stimulation in the muscles innervated by the motor nerve. The muscle can be stimulated by one or more flexible electrodes, which resemble the deep brain stimulation electrodes.

In an embodiment of present invention the device is made of a relatively soft material and is on the outside full with recording and stimulating electrodes. This is shown in FIGS. 7 *d* and *e*. that displays a transverse section of the spinal canal, T2-weighted MR-image. On the right side a device (black on the right-sided image) is drawn, which mimics perfectly part of the cavity filled with cerebrospinal fluid (white on the left-sided image).

The indication for such device can be to provide tingling sensations at the site of the chronic neuropathic pain or to restore one or more lesioned nerve roots or to diminish spasticity or restore bowel and bladder function. In FIG. 7 *e*. the device is smaller than in FIG. 7 *d*., but it is clear that the device can have any size, as long as it resembles the cavity filled with cerebro-spinal fluid. In both FIG. 7 *d* and *e* the cavity is part of the subarachnoid space around certain nerve roots of the cauda equina. These devices, covered with stimulating and recording electrodes can be connected via a computer with devices implanted around the spinal cord rostral (i.e. more located in the direction of the head) to a spinal cord injury or even in the spinal cord cavity (which was created by the spinal cord injury) or in the spinal cord itself, as depicted in FIG. 9. In this way motor information will be recorded in the more rostrally implanted electrodes, and stimulation can be done at the level of the more caudal device via the stimulating electrodes (which is implanted in the lesion cavity of the spinal cord, around the more caudally located spinal cord, around certain relevant nerve roots of the cauda equina, at the level of a peripheral nerve or in the muscle itself. For the sensory information the caudal recording electrodes are used and the information is sent via the computer to the stimulating electrodes of the more rostrally placed devices.

Sagittal transsection through the spinal canal, T2-weighted MR-images are shown in FIG. 7 *f*. The device is placed around the cauda equina, also based upon medical imaging. It is in fact the same device as in FIG. 7 *c*, but looked at it from a different angle (sagittal section instead of a transverse section). There are interactions between microelectrodes (stimulating and recording) at the edges between the nerve roots and the device, and the device has many holes. There should be no sharp edges at the upper and lower border of the device, in order not to damage the nerve roots of the cauda equina. Sometimes it can suffice to bridge only one or some nerve roots. The indication can be to bridge a damaged nerve root, or to perform nerve root stimulation as a treatment for chronic neuropathic pain or to bridge a spinal cord injury as explained above. The outer part of the device does not need to be a circle as depicted in figure FIG. 7 *c*, but is a 3D-structure, which is based upon medical imaging (especially T2-weighted MRI images), taking care not to compress any nerve roots or other tissues, especially not where the nerve roots are leaving the spinal canal, and the device should be as small as possible, so that it can move together with the nerve roots up and down when the patient is bending forward and backward, so that the microelectrodes remain in contact with the same axons in all positions.

An example of a device for recording and stimulation of the (either superior or inferior) colliculus and of the cerebellum is show in FIG. 7 *g*. The insertion can be done in a similar way as insertion of the balloon or balloon-like structure or the puzzle device or via the subarachnoid space via an open operation or via classical endoscopic techniques. It should be clear that those are only examples of possibilities. Everywhere at the edge between nervous tissue and other tissue, such a device can be placed. One can think of placing it there where cerebrospinal fluid is placed, but also one can resect bone which overlies the nervous tissue or push away fascia or muscle etc.

For spinal cord stimulation as a treatment for chronic neuropathic pain, exactly the same devices, which are on the market in the companies ANS and Medtronic Inc., can be produced, but now with many thousands to millions of electrodes, and the device should be flexible, e.g. produced in silicone as in our previous patent, and based upon the anatomy as visualized with medical imaging techniques as discussed above, patient by patient, and if the anatomy of the spinal cords of 2 patients look alike, then a similar electrode can be used in the 2 patients.

Example 8

Combination of Microelectrodes for Recording and Stimulation Together with Macroelectrodes for Stimulation In all discussed devices, the classical contacts of Medtronic design leads or ANS design leads can be added. Those contacts can enable to modulate the activity of nerve cells at a larger distance than by using the stimulating microelectrodes.

Therefore all previously discussed designs can be produced either as a combination of microelectrodes for recording and stimulation, or as a combination of microelectrodes for recording and stimulation together with macroelectrodes for stimulation. Those electrical contacts can be exactly similar to the contacts which are produced by companies like Medtronic and ANS, but can also be different in size and form. Especially interesting will be the contacts in FIG. 8.

The area between the outer circle and inner circle is the same metal as used in electrodes for nervous system stimulation which or nowadays on the market (FIG. 8). Within this area (i.e. within the smallest circle) and outside the outer circle between 1 and several thousands of microelectrodes for recording and stimulation can be placed. The contact can be any form (circle, oval, quadrangle, triangle etc. and some of those forms are depicted in the upper panel) and it has a flat structure. The wires for the microelectrodes can either run behind the contact, or at a pathway which runs through the large contact as depicted in the lower figures.

For all devices in this invention, it can be that after having made some models, based on medical imaging in several patients, it can turn out that some standard models of 3-D volumes fit in several patients, which eases the production process.

For all devices it holds that combination of several devices are possible, and that a stimulator (which records, stimulates and leads the information from recording electrodes and stimulating electrodes) connects 2 or more devices, interconnected by cables. For example, recording of motor cortex signals can steer directly stimulating electrodes in a motor pathway in the brain, brainstem, spinal cord or peripheral nerve or directly in the muscle. The opposite holds for the sensory system and similar applications can be thought of in the other systems of the nervous system.

The electronics required for the restoration of the nerve signal transduction path comprises electrodes for electrical stimulation of the nerve cells, electrodes for the recording of the neuronal electrical signals, signal amplification and filtering elements, AD convertors, pulse generators and eventually a wireless transmission block for external data transfer.

Example 9

Bringing Electronics on a 3D Object

There are alternative approaches for the realization of electronic circuits with a 3D shape:
  planar fabrication on flexible substrates (making use of conventional lithography)
  "curved" fabrication on already shaped 3D substrates (making use of spherical lithography)

The electrodes for recording and stimulation should be present on the implant in direct contact with the healthy tissue surrounding the lesion area. The implant is solid structure, or a balloon or balloon-like structure filed with fluid or solids, fitting relevant parts of the cavity. The signal amplification and filtering elements can be placed either directly in the very close vicinity of the recording elements, on the same side of the implant as the stimulation and recording elements (see FIG. 10A) or on the opposite side (see FIG. 11B) or at a certain distance away from the lesion below or above the dura matter (see FIGS. 12A and 12B).

FIG. 15 illustrates two possible packaging methods, i.e. wire bonding approach (left) and flip chip approach (right), for use with a probe according to the present invention. These methods can be used for producing foils that can be shaped imaging and rapid prototyping technology described in this application. The methods displayed in FIG. 15 have merely be described for a neuro-bridging device e.g. for restoring the interconnection between neural cells that has been disrupted by a cavity. However, it is to be understood that this is not limiting the invention and that other bridging device devices 20, such as bridging device devices 20 to be implanted in muscular tissue or in cardiac tissue for stimulating excitable cells within these tissues may also be manufactured using the method according to the invention. In a first step, an array of stimulation/recording pixels (or stimulation pixels and/or recording pixels) 51 is formed on a die 53, which may, for example, be a silicon die. Hereinafter, the method for the manufacturing of a bridging device 50 according to the first aspect of the invention will be described for a silicon die 53. It has to be understood that this is not limiting to the invention and that other semiconductor materials, such as e.g. GaAs, SOI (silicon on insulator), can also be used. However, in the case of SOI the method may be adapted in the sense that no thinning step may be needed as SOI can be made thin enough before the start of the manufacturing of the bridging device device 50. Formation of the stimulation/recording pixels (or stimulation pixels and/or recording pixels) 51 onto the die 53 may be performed by means of micro-fabrication techniques known by persons skilled in the art, such as, for example, IC or CMOS standard and non standard processes. The die 53 may have a thickness of between 300 μm and 1 mm, for example 850 μm. It is an advantage of the present invention that the array of stimulation/recording pixels (or stimulation pixels and/or recording pixels) 51 may be applied by a standard process on a standard substrate, as this makes the fabrication process far more easy than making the array of stimulating/recording sites directly on a substantially cylindrical or conical substrate. Contacts 54 are provided using, for example, standard CMOS metallisation processes. Suitable materials for forming the contacts 55 may, for example, be Al or Au or any other suitable noble metal. In a next step, the die 53 on which the array of stimulation/recording pixels (or stimulation pixels and/or recording pixels) 51 is formed may first be thinned down to e.g. 50 μm, preferably down to 55 μm, more preferably down to 10 μm and most preferably down to 5 μm. As already discussed, in case the die is formed of SOI, this thinning step may not be necessary because the SOI die may already be thin enough. In the case that the bridging device 50 would only comprise passive electrodes, e.g. metal lines, it could be processed on all kind of substrates including plastic. However, the signal to noise ration and thus the chronic recording will be poor with such electrodes. Also thin-film transistors have poorer properties compared to silicon transistors. Therefore, preferably standard CMOS processing performed on semiconductor substrates such as e.g. Si, GaAs or SOI substrates may be used according to embodiments of the present invention. Thinning down is performed down to a thickness of the die low enough to make the die flexible. Thinning down may be performed by any suitable method, such as e.g. mechanical or chemical polishing or by a combination of both. In a next step, the thinned die 53 comprising the stimulation/recording pixels (or stimulation pixels and/or recording pixels) 51 is bonded to a substrate 55. The substrate 55 may, for example, comprise biocompatible material such as any of parylene C, parylene N, polyimide, polysiloxane rubber or teflon, but may also comprise a noble metal (e.g. Au, Pt, Ir), titanium, oxides (e.g. IrOx, Ta2O5, SiO2, ZrO2), Si3N4 or biocompatible epoxies. The material the substrate 55 is formed of should be such that cytotoxicity and material degradation is prevented when the bridging device 50 is implanted in the tissue, for example the brain in case of a neuro-bridging device 50 e.g. for brain function restoration by bridging the brain signal gap canes by lesions. The substrate 55 has an area and lies in a plane, the area extending in the direction of its plane. The die 53 comprising the stimulation/recording pixels (or stimulation pixels and/or recording pixels) 51 also has an area, the area of the die 53 extending in a direction substantially parallel to the plane of the substrate 55. The area of the substrate 55 may preferably be larger than the area of the die 53 comprising the stimulation/recording pixels (or stimulation pixels and/or recording pixels) 51. The die 53 comprising the stimulation/recording pixels (or stimulation pixels and/or recording pixels) 51 forms the active part of the bridging device 50. The packaging or bonding method may be based on either wire bonding or flip chip assembly of the die 53 comprising the array of stimulation/recording pixels (or stimulation pixels and/or recording pixels) 51 onto the substrate 55, which is a biocompatible flexible substrate. By a process of 3D imaging of cavities in tissues or organs of a multicellular organism (e.g. a mammal or human) and producing a representing mold by rapid protype (as further described in this application) the substrate comprising the array of microelectrode pixels can subsequently be folded to acquire a shape that exactly fits into the cavity and presents the pixels at the edge of the cavity to healthy.

Planar Fabrication on Flexible Substrates:
An array in which each pixel includes stimulation and recording transducers can be used to control the electrical field distribution in three dimensions and to perform recordings of neuronal electrical activity with high spatial resolution and high signal-to-noise ratio. Such an array is fabricated by means of integrated circuit (IC) techniques either directly on biocompatible and flexible substrates (e.g. polyimides, polyurethane, parylene, polysiloxanes etc) or on classical silicon wafers. In the last approach, after the processing the silicon wafers are being attached on flexible substrates and after that thin down to few microns or tenths of microns.

Eventually the array can comprise separate pixels with al least one stimulating element and separate pixels with at least one recording element, or the array can comprise separate stimulating pixel zones or separate recording pixels zones.

The flexible foil containing the electronics will be further brought in a three dimensional shape using a molding approach. The mold will be designed according to the particularities of a given lesion.

The flexible foil containing the electronics will be further transformed to a three dimensional shape using a molding approach. Since the customized implant electrode has to fit exactly into the cavity, the mold will be designed according to the particularities of the given lesion. A digital model of the cavity is available by CT or MRI scans of the patient. Using appropriate software (such as the 3D Systems soft, VIDX Scan Imaging Software (Evex Analytical Instruments), Zmode, Vis5D, VIDA)), very fine details can be integrated in the digital design of the mold. Once the computer model of the mold is ready, the mold can be produced directly by layer manufacturing techniques, such as Selective Laser Sintering (SLS), Selective Laser Melting (SLM), Stereolithography (SLA), Fused Deposition Modeling (FDM), Inkjet based systems, Three Dimensional Printing (3DP), Laminated Object Manufacturing (LOM); Laser Engineered Net Shaping (TM) (LENS®) etc. These Rapid Manufacturing processes have the advantage of geometrical freedom and very small features can easily be made. Different materials are possible: a metal mold can be produced by SLS or a polymer, preferably PC-ISO Polycarbonate, mold can be produced by SLA. When using the molding strategy to produce the customized three dimensional electrode, two methods are possible. An external mold (FIG. 10) can be made for producing the three dimensional foil by casting or spraying or an internal mold (FIG. 10) can be made for producing the three dimensional foil by blowing.

Figure 13:
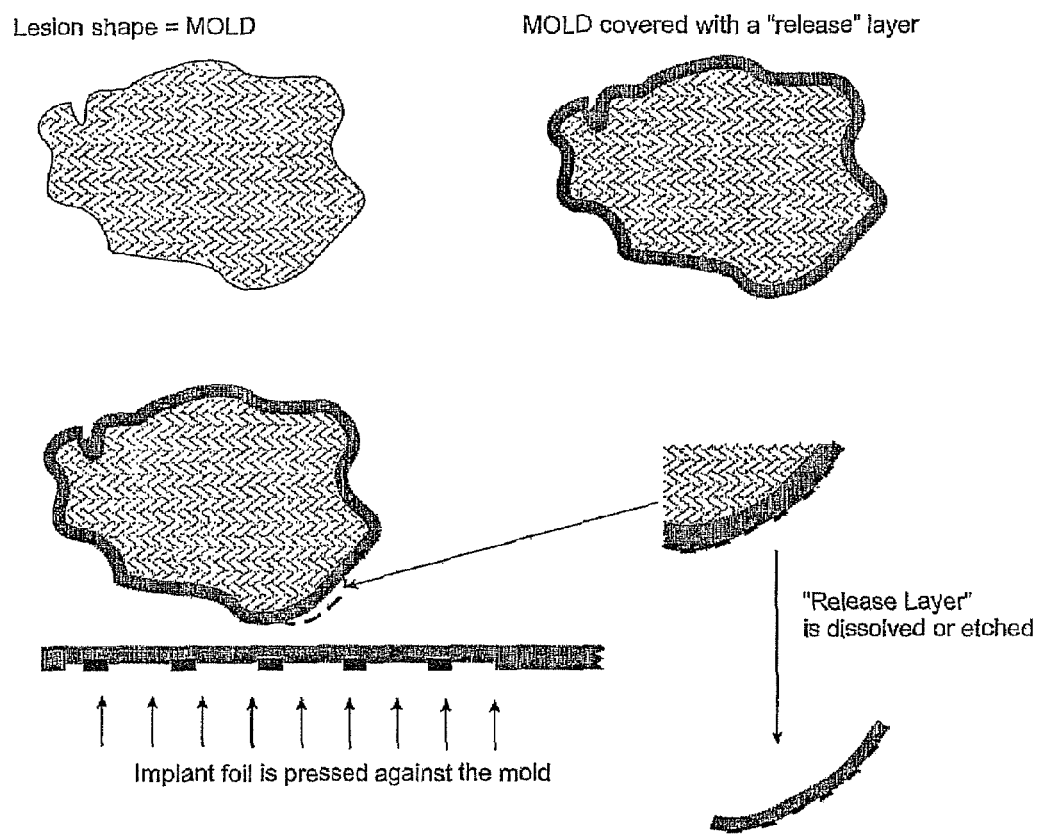

Alternative approaches can be used for the molding procedure:

Method 1: A mold, for instance a metal mold, with the exact configuration of the lesion is produced (see FIG. 13). The foil containing the electronics is pushed against the mold and subjected to a heat treatment that will deform the plastic foil. The mold is further released from the foil. To facilitate release, the mold can be eventually covered with a "sacrificial" release layer that will be dissolved or etched. Such a sacrificial release layer could be a thin metal layer (e.g. aluminium that is deposited by evaporation or sputtering directly onto the mold). After the thermal step, this layer is dissolved in the appropriate metal etchant (e.g. aluminium etch solutions).

Method 2: The mold, for instance metal mold, is covered conformally with a biocompatible polymer (e.g. parylene—vacuum sublimation; polyimide—spray coating etc). Subsequently a "glue" layer is dispersed conformally onto the biocompatible layer. The glue layer can be a polymeric material or an epoxy material (e.g. a photocurable epoxy or heat curable epoxy). The glue layer can be brought onto the mold by means of dip or spray coating. The foil containing the electronics is brought in contact and pressed against the coated mold. After adhesion, the foil is released from the mold. Again a sacrificial release layer can be used to facilitate the release process.

"Curved" Fabrication on Already Structured 3D Substrates:

Recently the fabrication of semiconductor devices and sensor on 1 mm-diameter spherical silicon substrates has been demonstrated [Takeda, Adv. Pack. Materials, 2001] (see FIG. 14). Ball Semiconductor Inc. has developed layout design tools and a special mask-less spherical lithographic technique suitable for spherical substrate processing. In this technique an 800×600 micro-mirror array create a spherical focal plane instead of a planar one. The pattern generation using the micro-mirror array is controlled electrically.

Also electron beam lithography can be used for the curved/non-flat substrates. Caltech has developed for NASA's Jet Propulsion Laboratory a technique based on electron-beam phase holograms writing into thin films of poly(methylmethacrylate) [Makes et. al. www.nasatech.com and NASA Tech Briefs, May 1999 Maker, Paul et al.]. The application of this technique to a concave or convex substrate involves the following steps: (1) establish a grid of points onto the substrate; (2) for each grid point determine the e-beam apparatus focus, rotation and deflection calibration values; (3) use depth of focus information to define depth zones; (4) partition the exposure pattern into subpatterns (one subpattern for each depth zone); (5) with the electron-beam apparatus expose each depth zone according to its subpattern.

These techniques can be customized and applied for the transfer of electrode patterns onto non-spherical objects having locally convex/concave surfaces with the condition that there is no abrupt change in the surface shape between adjacent points.

Present invention involves the following fabrication scheme:

1—Lesion mold production (a mold representing the cavity in the central nervous system);

2—Conformal coating of the mold first with a sacrificial release layer (as described above) followed by a biocompatible implant materials (e.g. polyimide, parylene, polyurethane etc);

3—Coating with a electron-beam resist or photoresist of the mold (e.g. poly(methylmethacrylate));

4—patterning of a surface of the coating, preferably patterning of the photoresist using either the mask-less approach of Bell Semiconductors or the e-beam lithography (in this way the electrode patterns are brought onto the substrate);

5—Deposition of the electrode material (e.g. Pt, Ir, Pt/Ir, Au, activated iridium oxide) by means of metal evaporation or sputtering;

6—Resist strip;

7—Once the electrodes are fabricated, the release layer will be dissolved and the mold removed.

The invention claimed is:

1. A device for electrical recording and electrical stimulating of neurons which device is a bridging device for restoring transfer of electrical stimuli or for creating an electrical signal connection between a first neuron in the central nervous system (CNS) and a remote second neuron in the CNS, between which interconnectivity has been interrupted by a cavity, the bridging device comprising:

a first array of pixels wherein pixels of the array comprise a recording means for electrical recording activity of a first neuron in the CNS and a second array of pixels wherein pixels of the array comprise a stimulation means for electrically stimulating a second neuron in the CNS, characterized in that the recording means and stimulation means are electrically connected such that a relevant recording by said recording means can induce a relevant stimulation by said stimulation means to bridge the gap interrupting the interconnection of electrical signals between the first and the second neuron.

2. The bridging device according to claim 1, wherein each pixel of the first array comprises a recording means and each pixel of the second array comprises a stimulation means.

3. The bridging device according to claim 1, wherein the first array of pixels and the second array of pixels are located on a die.

4. The bridging device according to claim 3, wherein said die is positioned on a substrate.

5. The bridging device according to claim 1, wherein the device is customized to a shape and dimension to fit said pixels to the wall of the target cavity in the CNS.

6. The bridging device according to claim 5, further characterized in that it is a puzzling device or balloon-like structure with shape and dimensions customized to the shape and dimensions of the target cavity.

7. The bridging device according to claim 4, wherein the substrate is flexible.

8. The bridging device according to claim 4, wherein the substrate has a first area and the die has a second area, wherein the first area is bigger than the second area.

9. A method of restoring the interconnectivity between a first neuron and a remote second neuron in the CNS comprising the step of placing a bridging device according to claim 1 within a cavity resulting from a lesion in the CNS, wherein said cavity interrupts the interconnectivity between a first neuron and a remote second neuron in the CNS.

10. The method according to claim 9, wherein nerve signal transduction is restored or wherein lost functions of the nervous system are repaired.

11. The method according to claim 9, wherein the nerve function in a spinal cord injury or in damaged nerve roots is restored.

12. The method according to claim 9, for treating a disorder selected from the group consisting of dyskenia, sensory and motor loss, urinary and faecal incontinence.

* * * * *